United States Patent
Nakamura

(10) Patent No.: US 6,476,851 B1
(45) Date of Patent: Nov. 5, 2002

(54) ELECTRONIC ENDOSCOPE

(75) Inventor: Shinichi Nakamura, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 08/999,329

(22) Filed: Dec. 29, 1997

(30) Foreign Application Priority Data

Dec. 27, 1996 (JP) .............................................. 8-350512
Oct. 31, 1997 (JP) .............................................. 9-300430

(51) Int. Cl.⁷ ................................................ H04N 9/07
(52) U.S. Cl. ............................. 348/65; 348/65; 348/340
(58) Field of Search ............................... 348/65, 68, 73, 348/251, 315, 340, 342; 359/654, 661, 773, 557; 600/109, 111; 358/460; 250/208.1; H04N 9/07

(56) References Cited

U.S. PATENT DOCUMENTS

| | | | |
|---|---|---|---|
| 3,709,582 A | * | 1/1973 | Walker ........................ 359/733 |
| 4,554,585 A | * | 11/1985 | Carlson ........................ 348/342 |
| 4,674,844 A | | 6/1987 | Nishioka |
| 4,755,029 A | * | 7/1988 | Okabe ........................ 359/654 |
| 5,177,605 A | * | 1/1993 | Takahashi et all. ............ 348/65 |
| 5,223,982 A | | 6/1993 | Suzuki |
| 5,430,475 A | * | 7/1995 | Goto et al. .................... 348/65 |
| 5,436,767 A | | 7/1995 | Suzuki |
| 5,489,940 A | * | 2/1996 | Richardson et al. ......... 348/315 |
| 5,682,203 A | * | 10/1997 | Kato .......................... 348/340 |
| 5,704,896 A | * | 1/1998 | Fukunishi et at. .......... 600/109 |
| 5,739,953 A | * | 4/1998 | Sato ........................... 359/557 |
| 5,873,828 A | * | 2/1999 | Fujio et al. ................. 600/439 |
| 6,201,574 B1 | * | 3/2001 | Martin ....................... 348/315 |
| 6,211,916 B1 | * | 4/2001 | Hawkins het al. .......... 348/340 |

FOREIGN PATENT DOCUMENTS

JP  1-218286  8/1989
JP  5-346556  12/1993

* cited by examiner

Primary Examiner—Nhon Diep
(74) Attorney, Agent, or Firm—Pillsbury Winthrop LLP

(57) ABSTRACT

An electronic endoscope includes an objective lens system in which chief rays directed toward the maximum image height are inclined outwardly with respect to the optical axis and a solid-state image sensor which has a light-receiving surface on which many pixels are arrayed and which provides a light beam inclined outwardly with respect to the optical axis and incident on the light-receiving surface with a higher power, in separating from the center of the light-receiving surface, than a light beam incident perpendicularly on the light-receiving surface. In doing so, distortion is favorably corrected and shading can be prevented.

21 Claims, 14 Drawing Sheets

SPHERICAL ABERRATION
F/3.78

-0.05    0.05

ASTIGMATISM
IH 1.00

-0.1    0.1

DISTORTION

-50.0  (%)  50.0

FIG. 15
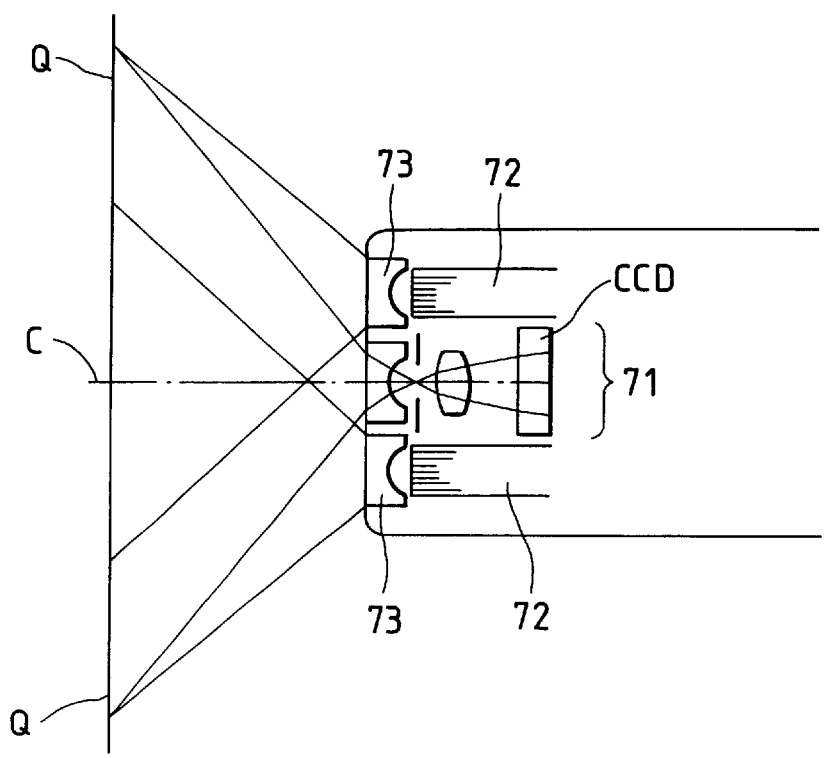
FIG. 16A        FIG. 16B        FIG. 16C
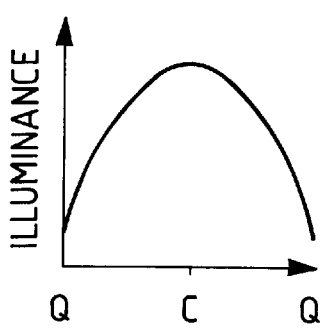 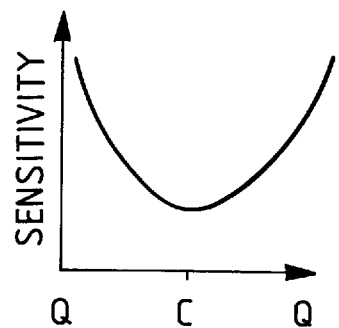 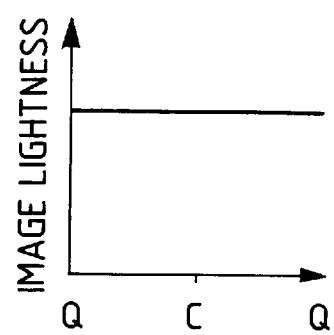

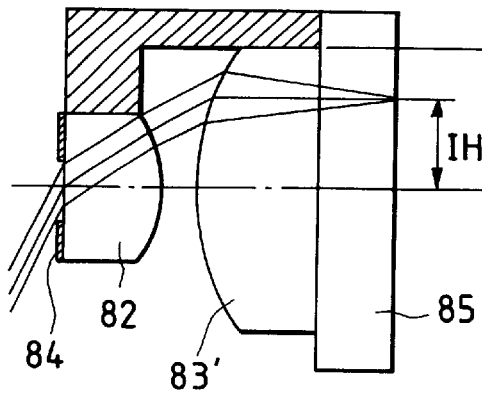 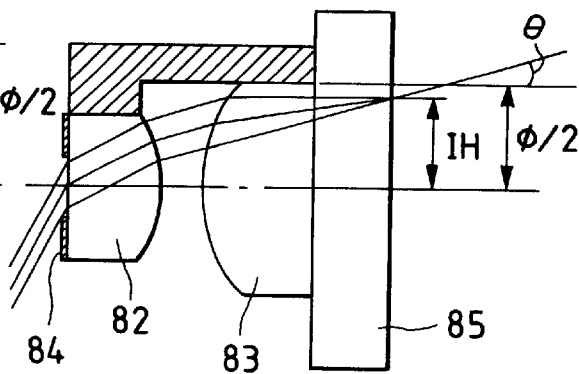
FIG. 19A    FIG. 19B
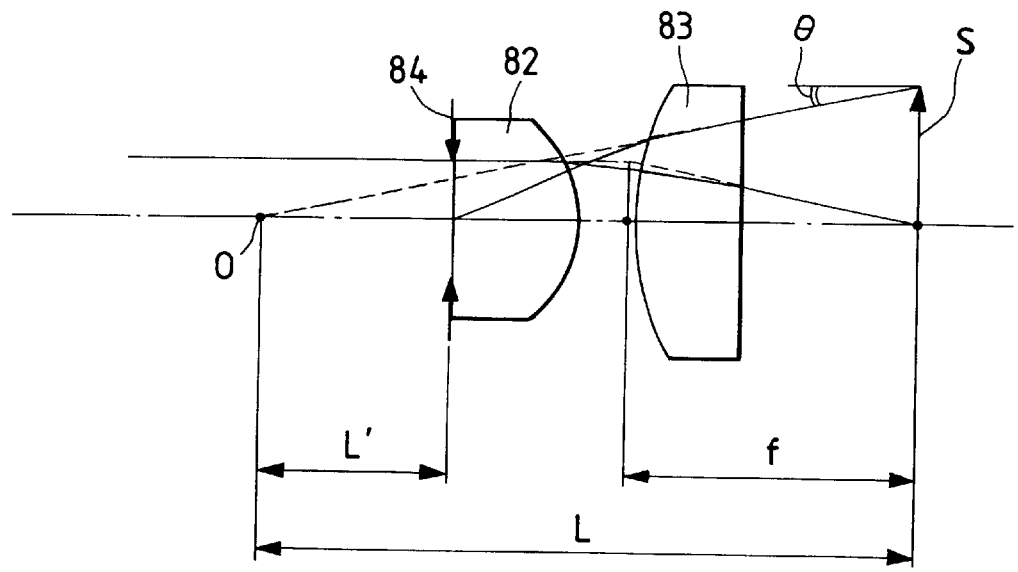
FIG. 20

ELECTRONIC ENDOSCOPE

BACKGROUND OF THE INVENTION

1. Field of the Invention

This invention relates to an electronic endoscope in which provisions are made to correct for distortion and prevent shading.

2. Description of Related Art

In recent years, An endoscope whose elongated, insertable section is inserted in a narrow tubular cavity or human body to observe an organ has come into prominent use. In particular, an electronic endoscope is often used in which a solid-state image sensor, such as a CCD (charge coupled device), is placed at the distal end or ocular section of the endoscope so that observations can be made through a monitor.

In keeping with an increase of the number of pixels arrayed on the light-receiving surface of the CCD, a compact design of the CCD has recently been developed. Consequently, the problem is raised that off-axis chief rays of light passing through the objective lens system of the electronic endoscope are incident on pixels different from those on which they are naturally expected to be incident and proper colors are not reproduced. This phenomenon is called color shading.

FIG. 1 shows a positional relationship between a photosensor and a microlens in a conventional CCD. In this figure, reference symbols $P_1$ and $P_2$ represent chief rays emanating from an exit pupil 0 toward the CCD. Consider now the case where the chief ray $P_1$ is incident on one photosensor, situated close to the optical axis, of the CCD and the chief ray $P_2$ is incident on another photosensor, located farther from the optical axis, of the CCD. The chief ray $P_1$ passes through a microlens $A_m$ and enters a photosensor $B_m$ located opposite thereto. The chief ray $P_2$, however, after passing through a microlens $B_n$, fails to enter a photosensor $B_n$ located opposite thereto. In this way, the photosensor $B_n$, located farther from the optical axis, of the CCD may give rise to the phenomenon that a marginal beam of light is eclipsed and thus an image to be formed becomes dark. This phenomenon is called luminance shading. In the following description, the term "shading" refers to both the color shading and the luminance shading.

In the electronic endoscope, such shading is attributable to the fact that some of rays passing through the objective lens system are incident obliquely on the photosensors of the CCD.

Thus, in order to solve this problem, for example, Japanese Patent Preliminary Publication No. Hei 1-218286 proposes an apparatus in which a field lens is interposed between the objective lens system and the CCD so that rays, emerging from the objective lens system are incident almost perpendicularly on the CCD.

In general, the objective lens system used in the endoscope has a large angle of view so that a wide field can be observed, and hence is exceedingly subject to distortion.

Thus, an endoscope; objective proposed as an objective lens system designed to favorably correct for distortion is disclosed in Japanese Patent Preliminary Publication Sho 61-35414. This endoscope objective is composed of four lens units and has the feature that tile lens unit located closest, to the image side includes a meniscus lens.

Since the objective includes the meniscus lens, the entire length of the objective is increased accordingly. If the meniscus lens can be removed, the entire length of this lens system will be reduced. FIG. 2 shows an objective lens system constructed with three lens units for such a purpose. This objective lens system, however, encounters the difficulty that, in order to render emerging light incident normally on the CCD for the purpose of preventing shading, the diameter of the rear lens unit must be enlarged.

However, where the endoscope is used, notably for medicine, it is favorable to minimize the diameter of the insertable section and the length of a rigid portion at the distal end where the objective lens system is placed, in order to reduce pain caused to a patient when the endoscope is inserted and to facilitate the insertion thereof. The objective lens system which has the smallest possible diameter and the minimum length is suitable for use in the endoscope.

An objective lens system proposed to achieve this object is disclosed in Japanese Patent Preliminary Publication No. Hei 5-107470. This objective lens system is constructed with three lenses so that the field lens is removed to thereby diminish the diameter and entire length of the objective lens system and aberrations are favorably corrected.

However, the endoscope objective set forth in Sho 61-35414 mentioned above, although it is possible to correct for distortion, cannot render all beams of light emerging from this objective incident normally on the CCD, thus bringing about shading.

The objective lens system disclosed in Hei 5-107470 cannot prevent shading for a similar reason.

More recently, on the other hand, a CCD such as that disclosed in, for example, Japanese Patent Preliminary Publication No. Hei 5-346556 is proposed in which the positions of microlenses arranged opposite to respective photosensors are shifted closer to the optical axis than those of the photosensors, and thereby the production of shading is obviated. Where such a CCD is used, it is not necessary to make provision for preventing the shading on the objective side.

In this way, the CCD in which provision is made to prevent shading is most suitable for use in the endoscope, but no cases have as yet arisen in which this CCD has been used in the endoscope.

SUMMARY OF THE INVENTION

It is, therefore, a primary object of the present invention to provide an electronic endoscope in which distortion is favorably corrected and provision is made to prevent shading.

It is another object of the present invention to provide an electronic endoscope in which the compactness of the objective lens system is intended to minimize the diameter of the insertable section and the length of a rigid portion at the distal end of the endoscope.

In order to achieve the above objects, according to one aspect of the present invention, the electronic endoscope is equipped with an objective lens system in which chief rays directed toward the maximum image height are inclined outwardly with respect to the optical axis and a solid-state image sensor which has a light-receiving surface on which many pixels are arrayed and which provides a light beam inclined outwardly with respect to the optical axis and incident on the light-receiving surface with a higher power, in separating from the center of the light-receiving surface, than that incident normally on the light-receiving surface.

According to another aspect of the present invention, the electronic endoscope includes a plurality of objective lens systems, each of which is constructed so that chief rays directed toward the maximum image height are inclined outwardly with respect to the optical axis, and a solid-state image sensor which has a single light-receiving surface on which many pixels are arrayed so that images formed by the plurality of objective lens systems are received by this single light-receiving surface. The solid-state image sensor is such that, in separating from the center of each of the images formed on the single light-receiving surface by the plurality of objective lens systems, a light beam inclined outwardly with respect to the optical axis and incident on the single light-receiving surface is provided with a higher power than a light beam incident normally on the single light-receiving surface.

According to still another aspect of the present invention, the electronic endoscope is equipped with an objective lens system, illumination optical systems possessing such light-distribution characteristics that illuminance on the periphery of the visual field of the objective lens system is lower than that at the center thereof, and a solid-state image sensor in which, when light of uniform intensity is incident on the light-receiving surface thereof, each of pixels located on the periphery of the light-receiving surface produces a higher power than that located at the center thereof.

These and other objects as well as the features and advantages of the present invention will become apparent from the following detailed description of the preferred embodiments when taken in conjunction with the accompanying drawings.

BRIEF DESCRIPTION OF THE DRAWINGS

FIG. 15 is a sectional view an optical arrangement at the distal end of the insertable section of the electronic endoscope of a seventh embodiment in the present invention;

FIG. 16A is a graph showing light-distribution characteristics of illumination systems in the electronic endoscope of the seventh embodiment;

FIG. 16B is a graph showing the light-sensitivity distribution of a CCD in the electronic endoscope of the seventh embodiment;

FIG. 16C is a graph showing the brightness of an image derived from the electronic endoscope of the seventh embodiment;

FIG. 19A is a view showing the case where a lens diameter is enlarged in the conventional electronic endoscope;

FIG. 19B is a view for explaining the repair of a defect of FIG. 19A in the eighth embodiment;

FIG. 20 is an explanatory view for setting the angle of inclination of a chief ray at, 10–30°;

DETAILED DESCRIPTION OF THE PREFERRED EMBODIMENTS

Figure 1:
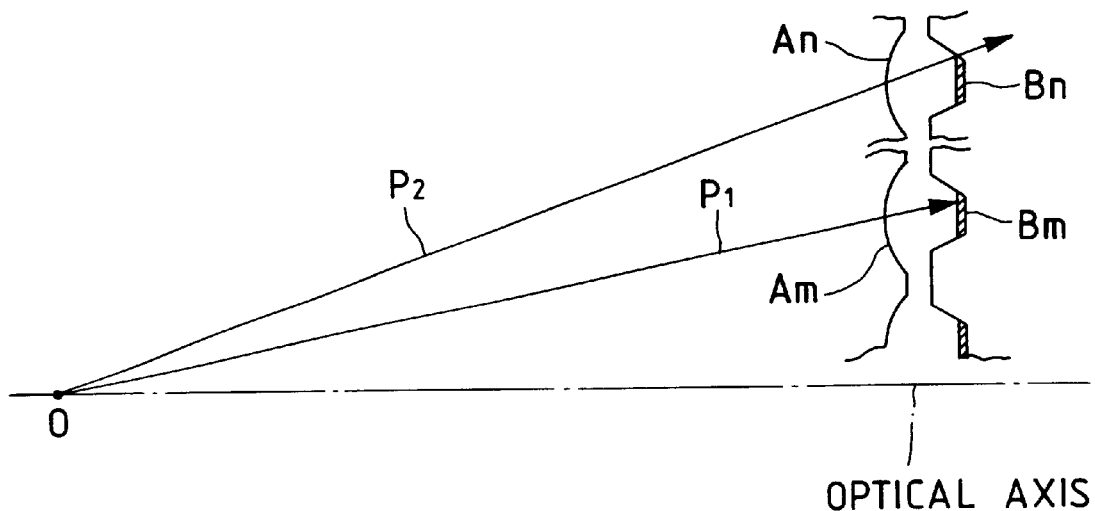
FIG. 1 is a sectional view showing the configuration of photosensors and microlenses placed immediately therebefore in a conventional CCD.
Figure 2:
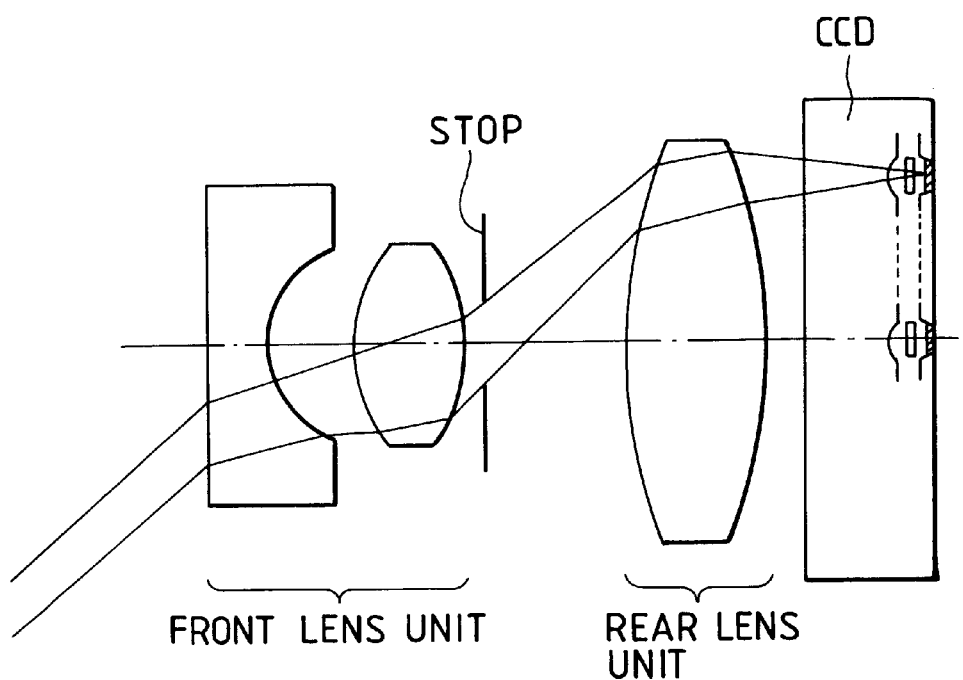
FIG. 2 is a sectional view showing the arrangement, developed along the optical axis, of a conventional objective lens system having the function of prevention of shading.

In accordance with the embodiments shown in the drawings, the present invention will be explained in detail below.

First Embodiment

Figure 3:
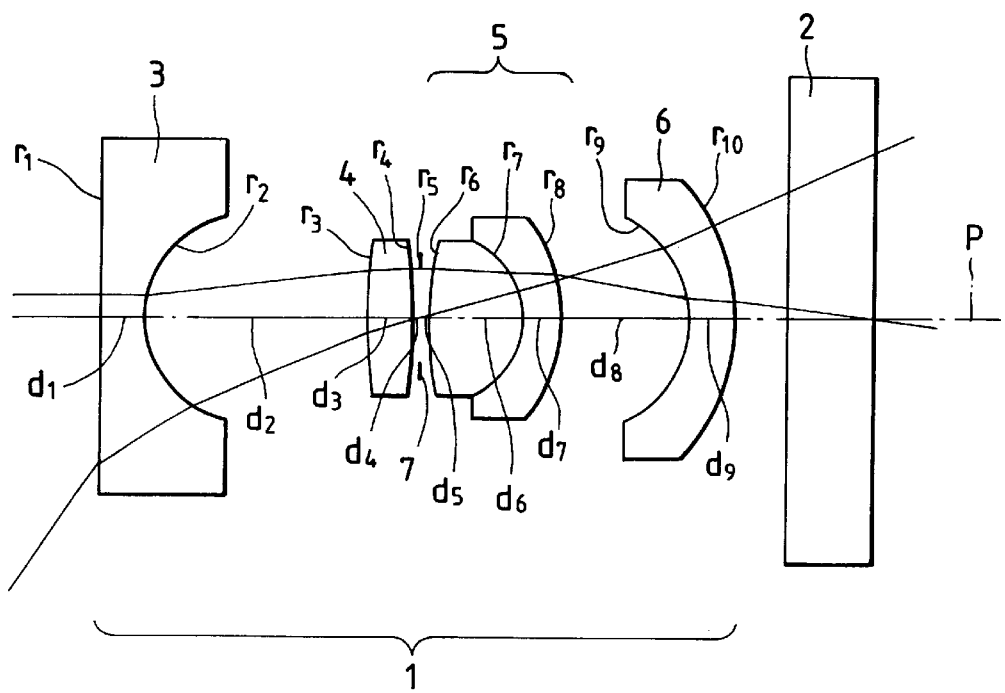
FIG. 3 is a sectional view showing the arrangement, developed along the optical axis, of an objective system placed in a rigid portion at the distal end of the insertable section of the electronic endoscope of a first embodiment in the present invention.

The objective system of the electronic endoscope in this embodiment, as shown in FIG. 3, is constructed with an objective lens system 1 and a CCD 2 which is placed on the light-emergence side thereof. The objective lens system 1 includes, in order from the object side not shown, a first lens unit 3 of a negative lens, a second lens unit 4 of a positive lens, a third lens unit 5 of a positive cemented lens, and a fourth lens unit 6 of a meniscus lens having the concave surface on the object side. An aperture stop 7 is interposed between the second lens unit 4 and the third lens unit 5.

In the electronic endoscope of the first embodiment, the meniscus lens with a concave[s]urface directed toward the object side is used in the fourth lens unit 6 placed closest to the image side, of lens components constituting the objective lens system 1. It is thus intended to solve the problems that the entire length is increased, the lens diameter is enlarged, and considerable distortion is produced which are defects of the objective lens system of a retrofocus type in the endoscope. In the first embodiment, the diameters of the lens components constituting the objective lens system 1 are designed to diminish compared with the short side of the CCD 2. Moreover, the placement of the aperture stop 7 between the second lens unit 4 and the third lens unit 5 facilitates correction for distortion.

Here, when h1 and h4 denote the averages of heights of a chief ray at the lens surfaces of the first and fourth lens units 3 and 6, respectively; f1 and f4 denote focal lengths of the first and fourth lens units 3 and 4, respectively; R3 denotes the radius of curvature of the lens surface, closest to the object side, of the third lens unit 5; and f denotes the focal length of the whole of the objective lens system 1, it is desirable that the objective lens system 1 satisfies the following conditions:

$$|h_1/f_1| > 1.15 \times |h_4/f_4| \quad (1)$$

$$R_3 < 5f \quad (2)$$

Eq. (1) defines a condition for diminishing the diameters of lenses constituting the objective lens system 1 and for favorably correcting for distortion. The term $|h_1/f_1|$ indicates the refracting power of the chief ray in the first lens unit 3 and $|h_4/f_4|$ indicates the refracting power of the chief ray in the fourth lens unit 6. In Eq. (1), the value of $|h_1/f_1|$ is defined to become larger than that of $|h_4/f_4|$. In this way, the first lens unit 3 is made to have a wide angle of view, and the fourth lens unit 6 is corrected for distortion in such a way that the chief ray is moderately deflected and the amount of marginal light is not very small. Thus, the entire length of the objective lens system 1 (a distance from the first surface to an image plane) and the diameters of individual lenses are diminished.

Eq. (2), on the other hand, specifies a condition for correcting for spherical aberration. If the condition of Eq. (2) is not satisfied, spherical aberration will not be completely corrected.

In view of the use of the objective lens system 1 in the endoscope, it is desirable that its angle of view is kept to a maximum, preferably at least 100°. The vignetting factor of the objective lens system 1 relative to the light beam directed toward the maximum image height is less than 1. For the angle of inclination of the chief ray of the objective lens system 1, it is desirable that the chief ray makes about 10–30° with the optical axis. If it is smaller than 10°, distortion will not be completely corrected, while if it is larger than 30°, shading will not be completely obviated.

The following is numerical data of individual optical members constituting the objective lens system 1 used in the electronic endoscope of the first embodiment.

f = 1.00, F-number = 3.78, Image height = 1.0040, Angle of view = 115°

$r_1 = \infty$
$\quad d_1 = 0.2520 \quad n_1 = 1.51633 \quad v_1 = 64.15$
$r_2 = 0.6655$
$\quad d_2 = 1.2601$
$r_3 = 2.2444$
$\quad d_3 = 0.2520 \quad n_3 = 1.74100 \quad v_3 = 52.68$
$r_4 = -6.8676$
$\quad d_4 = 0.0504$
$r_5 = \infty$ (the aperture stop 7)
$\quad d_5 = 0.0504$
$r_6 = 2.5764$
$\quad d_6 = 0.5544 \quad n_6 = 1.62041 \quad v_6 = 60.27$
$r_7 = -0.5040$
$\quad d_7 = 0.2016 \quad n_7 = 1.80518 \quad v_7 = 25.43$
$r_8 = -0.9738$
$\quad d_8 = 0.7436$
$r_9 = -0.6990$
$\quad d_9 = 0.2520 \quad n_9 = 1.72825 \quad v_9 = 28.46$
$r_{10} = -1.2601$ $h_1/f_1 = 0.541$, $h_4/f_4 = 0.184$
$(h_1/f_1)/(h_4/f_4) = 2.94$
$f_1 = -1.29$, $f_{23}$ (the combined focal length of the second and third lens units) = 1.08, $f_4 = -2.66$ In the numerical data of the embodiment mentioned above, $r_1, r_2, \ldots$ represent radii of curvature of individual lens or member surfaces; $d_1, d_2, \ldots$ represent thicknesses of individual lenses or members, or spaces therebetween; $n_1, n_2, \ldots$ represent refractive indices of individual lenses or members; and $\nu_1$, $\nu_2$, . . . represent Abbe's numbers of individual lenses or members (The same holds for the lens data of the embodiments which will follow).

Figure 4A:
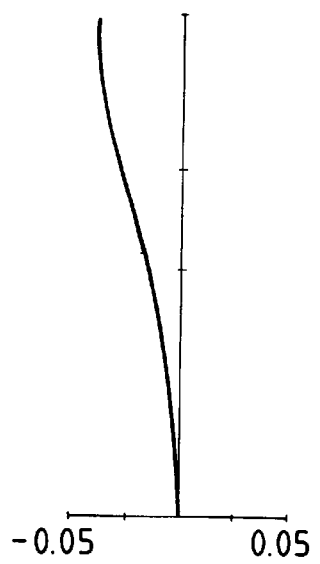
FIGS. 4A, 4B, and 4C are diagrams showing aberration characteristic curves of an objective lens system in FIG. 3.
Figure 4B:
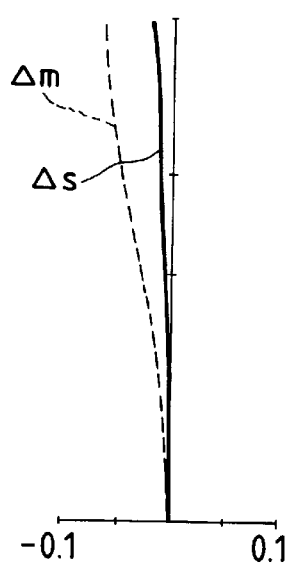
Figure 4C:
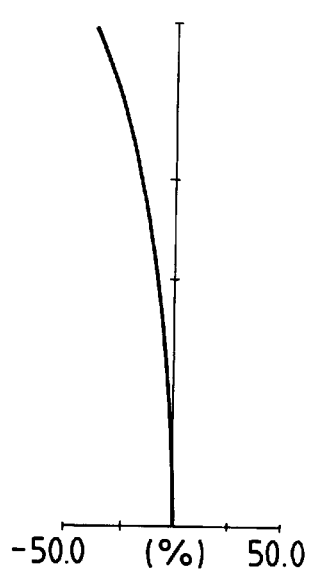

Aberration characteristics of the objective lens system 1 are as shown in FIGS. 4A–4C.

On the other hand, when distortion is corrected by the lens system itself, the angle of emergence of the ray emerging therefrom has a tendency to increase. As the angle of emergence of the ray from the objective lens system 1 increases, shading becomes more pronounced. Thus, in order to avoid such a difficulty, the electronic endoscope of the first embodiment is designed so that provision for preventing the shading is made in the CCD 2.

Figure 5:
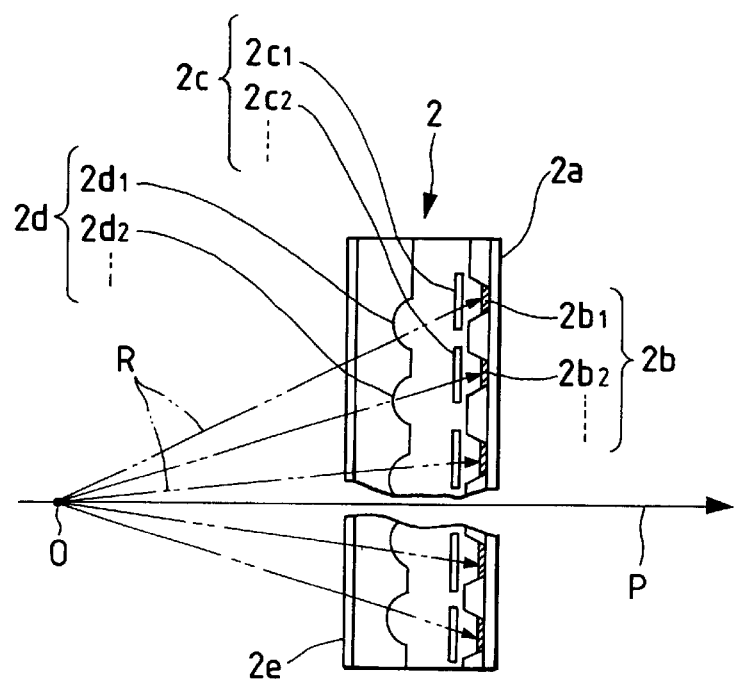
FIG. 5 is a sectional view schematically showing the configuration of a CCD in FIG. 3.
Figure 6:
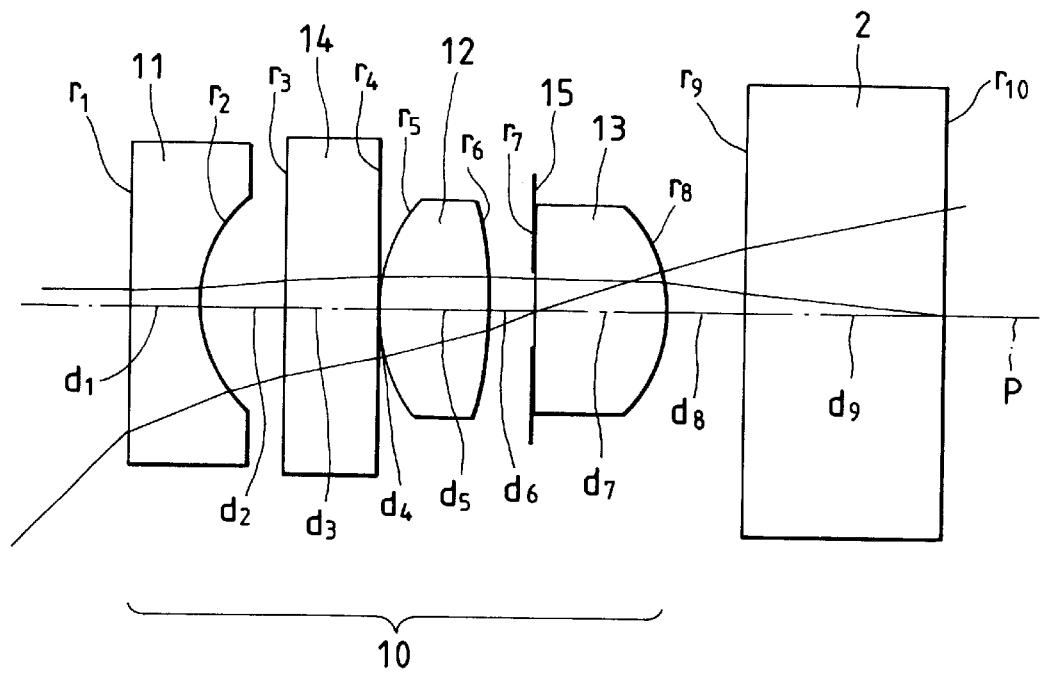
FIG. 6 is a sectional view showing the arrangement, developed along the optical axis of an objective system placed in a rigid portion at the distal end of the insertable section of the electronic endoscope of a second embodiment in the present invention.

FIG. 5 shows schematically the configuration of the CCD 2 used in the electronic endoscope of the first embodiment. The CCD 2 is integrally constructed by laminating, in order, a photosensor section 2b comprising photosensors $2b_1$, $2b_2$, . . . , $2b_n$ arranged longitudinally and laterally on a substrate 2a; a color filter section 2c comprising color filters $2c_1$, $2c_2$, . . . , $2c_n$ arranged longitudinally and laterally; a microlens section; 12d comprising microlenses $2d_1$, $2d_2$, . . . , $2d_n$ arranged in the same way; and a glass cover 2e.

In particular, the CCD 2 is such that, in separating from an optical axis P of the objective lens system 1, the positions of the microlenses $2d_1$, $2d_2$, . . . , $2d_n$ arranged opposite to the photosensors $2b_1$, $2b_2$, . . . $2b_n$ and the color filters $2c_1$, $2c_2$, . . . , $2c_n$ are shifted closer to the optical axis P than those of the photosensors and color filters. Specifically, the CCD 2 is constructed so that, in separating from the optical axis P of the objective lens system 1 along the light-receiving surface thereof, a shift between the center of each photosensor and color filter and the optical axis of each microlens placed opposite thereto increases progressively toward the optical axis P.

This construction enables chief rays R emanating from the exit pupil 0 of the objective lens system to be surely incident through the microlenses on the color filters and photosensors arranged opposite thereto, and the color shading and the luminance shading to be prevented. Consequently, the CCD 2 produces a higher power in the case where the light is incident obliquely on the light-receiving surface than in the case where it is incident normally thereon. This tendency becomes more pronounced in going to the periphery.

However, when distortion is corrected, even though the above-mentioned provision has been made with respect to the CCD 2, photo-sensors located on the periphery of the CCD 2, in contrast with those located close to the optical axis, have a tendency that the numerical aperture relative to incident light becomes small (namely, the vignetting factor is less than 1). As a result, the problem may arise that the amount of light incident on the photosensors located on the periphery decreases and an image formed becomes dark (namely, the same phenomenon as the luminance shading is produced).

Thus, the CCD 2 used in the electronic endoscope of the first embodiment may also be designed so that, in separating from the center of the light-receiving surface (which coincides with the optical axis of the objective lens system 1), the photosensor can produce a higher power. That is, the photosensor having a tendency to receive light incident obliquely is made higher in power than that receiving light incident almost perpendicularly. By doing so, it becomes possible to prevent the luminance shading in the CCD 2.

As mentioned above, the electronic endoscope of the first embodiment is capable of favorably correcting for distortion and surely preventing the shading.

Second Embodiment

In this embodiment, for the purpose of further reducing the entire length of the objective system, the objective lens system is constructed with three lens components by eliminating the field lens. he objective system of the electronic endoscope of the second embodiment, as shown in FIG. 16, comprises an objective lens system 10 and the CCD 2 placed on the light-emergence side thereof. The objective lens system 10 includes, in order from the object side, a first lens unit 11 of a negative lens, a second lens unit 12 of a positive lens, and a third lens unit 13 of a positive lens. Between the first lens unit 11 and the second lens unit 12, an infrared cutoff filter or laser cutoff filter 14 is interposed, when necessary. An aperture stop 15 is provided on the light-incidence surface of the third lens unit 13. The CCD 2 is the same as that used in the electronic endoscope of the first embodiment which has the function of prevention of shading.

The electronic endoscope of the second embodiment is such that, in the objective lens system 10, the aperture stop 15 is interposed between the second lens unit 12 and the third lens unit 13, and thereby it is only necessary that at least one lens with a positive refracting power (the second lens unit 12) is disposed on the object side of the aperture stop 15. Thus, chromatic aberration of magnification introduced by the first lens unit 11 with a negative refracting power is produced in such a way that this aberration is corrected by the second lens unit 12 with a positive refracting power, and thereby can be eliminated. In this way, the objective lens system 10 does away with the need for a cemented lens which has been used for correction for chromatic aberration of magnification, so that the arrangement of the lens system is simplified. Furthermore, by placing the second lens unit 12, the aperture stop 15, and the third lens unit 13 close to one another, the lens diameters of the second and third lens units 12 and 13 can be diminished.

The following is numerical data of individual optical members constituting the objective lens system 10 used in the electronic endoscope of the second embodiment.

--- f (the focal length of the objective lens system 10) = 1.001,
F-number = 3.833, Angle of view = 100°

$r_1 = \infty$
    $d_1 = 0.4984$    $n_1 = 1.88300$    $\nu_1 = 40.78$
$r_2 = 1.2048$
    $d_2 = 0.5708$
$r_3 = \infty$
    $d_3 = 0.6431$    $n_3 = 1.51633$    $\nu_3 = 64.15$
$r_4 = \infty$
    $d_4 = 0.0322$
$r_5 = 1.3000$
    $d_5 = 0.7464$    $n_5 = 1.51728$    $\nu_5 = 69.56$
$r_6 = -3.0866$
    $d_6 = 0.2912$
$r_7 = \infty$ (the aperture stop 15)
    $d_7 = 0.9419$    $n_7 = 1.51728$    $\nu_7 = 69.56$
$r_8 = -1.0736$
    $d_8 = 0.5266$
$r_9 = \infty$
    $d_9 = 1.6077$    $n_9 = 1.51633$    $\nu_9 = 64.15$
$r_{10} = \infty$

---

By the above arrangement, the electronic endoscope of the second embodiment is capable of diminishing the entire length and diameter of the objective system, and thus it can be intended to minimize the length of the rigid portion at the distal end as well as the diameter of the insertable section. Moreover, shading can be obviated.

Third Embodiment

In any endoscope, not to speak of the electronic endoscope, its elongated insertable section must be inserted in a narrow tubular cavity or human body, and hence it is desired to minimize the diameter of the insertable section. Additionally, in order to facilitate the insertion thereof for a bent part and relieve pain caused to a patient in the endoscope for medicine, it is also desired to reduce the length of the rigid portion at the distal end of the insertable section.

To meet these demands, the electronic endoscope, in particular, requires a more compact design of a solid-state imager disposed at the distal end or ocular section thereof, that is, compactness of the CCD. However, the compactness of the CCD causes its pixel size to be diminished and makes the area of the photosensor section of the CCD small. Consequently, the problem is encountered that the amount of light which is necessary for entering the image area of the CCD to form an object image is decreased and the output level of a signal is gradually lowered. As such, there is a limit to the compactness of the CCD.

Thus, in the electronic endoscope of the third embodiment, the CCD is placed horizontally along the longitudinal direction of the insertable section of the endoscope to thereby intend diminishing the diameter of the insertable section.

Figure 7A:
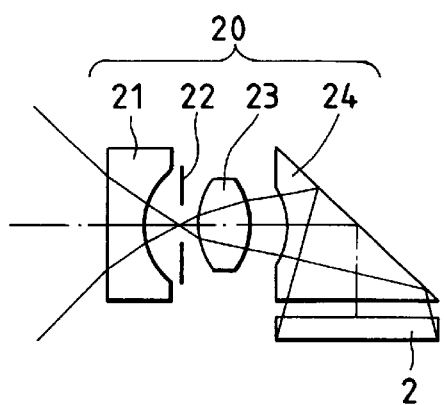
FIG. 7A is a sectional view showing an arrangement, developed along the optical axis, of an objective system placed in a rigid portion at the distal end of the insertable section of the electronic endoscope of a third embodiment in the present invention.
Figure 7B:
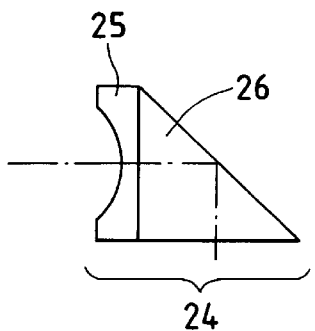
FIG. 7B is a view showing another example of a reflecting prism in FIG. 7A.

In FIG. 7A, the objective system of the electronic endoscope of the third embodiment comprises, in order from the object side, an objective lens system 20 and the CCD 2 which is placed horizontally, on the light-emergence side thereof, along the longitudinal direction of the insertable section of the endoscope. The objective lens system 20 includes, in order from the object side, a first lens unit 21 of a negative lens, an aperture stop 22, a second lens unit 23 of a positive lens, and a reflecting prism 24 with a concave surface directed toward the object side and a negative refracting power. The CCD 2 is the same as that used in the first embodiment, which has the function of prevention of shading. The reflecting prism 24, although the surface of incidence of light from the second lens unit 23 is configured as a concave surface, may be made, as shown in FIG. 7B, by cementing a negative lens 25 having a concave surface directed toward the object side to a reflecting prism 26.

Since, as in the foregoing, the objective lens system 20 provided in the electronic endoscope of the third embodiment has a concave surface (of a negative power) located closest to the image side, distortion can be favorably corrected. Furthermore, the CCD 2 having the function of prevention of shading is placed, and thus there is not any fear of producing the shading. In addition, the optical axis is bent through 90° by the reflecting prism 24, so that the CCD 2 can be placed Horizontally along the longitudinal direction of the insertable section of the endoscope.

Hence, in the electronic endoscope of the third embodiment, the optical axis of the objective lens system 20 is bent so that the CCD 2 is juxtaposed with the objective lens system 20, and thus the length of the rigid portion at the distal end can be reduced accordingly. At the same time, it is possible to intend diminishing the diameter of the insertable section. Moreover, the production of shading is avoidable.

Figure 8A:
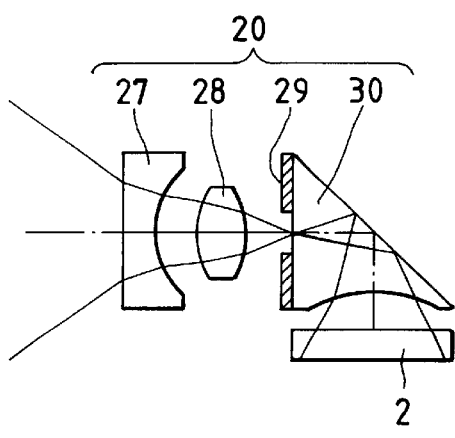
FIG. 8A is a sectional view showing another arrangement, developed along the optical axis, of an objective system placed in a rigid portion at the distal end of the insertable section of the electronic endoscope of the third embodiment in the present invention.
Figure 8B:
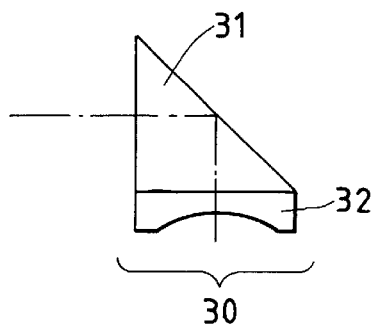
FIG. 8B is a view showing another example of a reflecting prism in FIG. 8A.

The objective lens system 20 may also be arranged as shown in FIG. 8A. Specifically, the objective lens system 20 may be designed to include, in order from the object side, a first lens unit 27 of a negative lens, a second lens unit 28 of a positive lens, an aperture stop 29, and a reflecting prism 30 whose exit surface is concave, having a negative refracting power. Thus, even when the reflecting prism 30 whose exit surface is concave is used, this objective system brings about the same effect as in that of the electronic endoscope shown in FIG. 7A. Also, the reflecting prism 30 is such that the prism itself has the negative refracting power, but as shown in FIG. 8B, it can also be made in such a way that an ordinary reflecting prism 31 is cemented to a negative lens 32 with the convex surface directed toward the light-emergence side.

Figure 9:
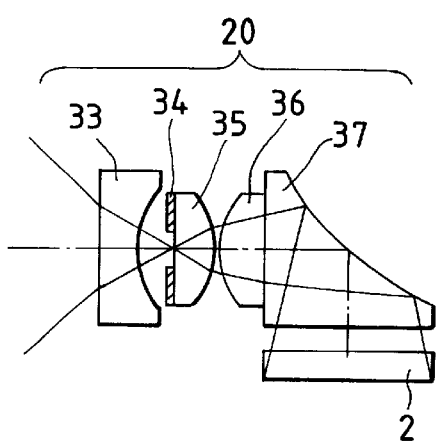
FIG. 9 is a sectional view showing still another arrangement, developed along the optical axis, of an objective system placed in a rigid portion at the distal end of the insertable section of the electronic endoscope of the third embodiment in the present invention.

Furthermore, the objective lens system 20 may well be arranged as shown in FIG. 9. That is, the objective lens system 20 may be designed to include, in order from the object side, a first lens unit 33 of a negative lens, an aperture stop 34, a second lens unit 35 of a positive lens, a third lens unit 36 of a positive lens, and a reflecting prism 37 cemented to the exit surface of the third lens unit 36, having a reflecting surface configured as a concave surface. In this way, even when the reflecting surface of the reflecting prism 37 is configured as the concave surface and the negative refracting power is provided there, this objective system brings about the same effect as that of the electronic endoscope in FIG. 7A.

Figure 10:
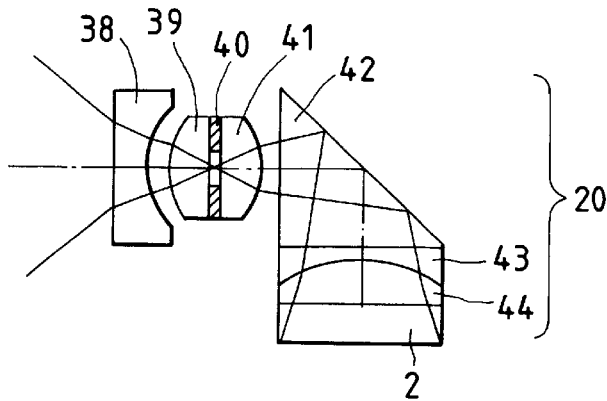
FIG. 10 is a sectional view showing a further arrangement, developed along the optical axis, of an objective system placed in a rigid portion at the distal end of the insertable section of the electronic endoscope of the third embodiment in the present invention.

FIG. 10 shows a further modification example of the objective system of the electronic endoscope in FIG. 7A. In this example, the objective lens system 20 include, in order from the object side, a first lens unit 38 of a negative lens; a second lens unit 39 of a positive lens; an aperture stop 40; a third lens unit 41 of a positive lens; a reflecting prism 42; a negative lens 43 cemented to the exit surface of the reflecting prism 42, having an exit surface configured as a concave surface; and a positive lens 44 cemented to the concave surface of the negative lens 43. In particular, between the negative lens 43 and the positive lens 44, settings are made so that the negative refracting power of the negative lens 43 becomes higher than the positive refracting power of the positive lens 44, thereby providing the negative and positive lenses 43 and 44 with a negative refracting power as a whole. Even with such an arrangement, the negative refracting power is provided on the rearmost side of the objective lens system, and distortion can be favorably corrected.

Fourth Embodiment

Figure 11:
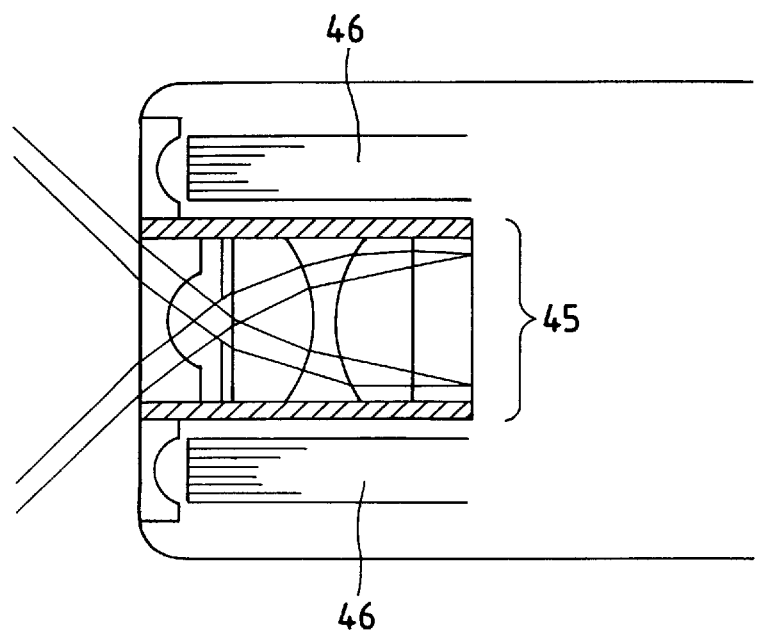
FIG. 11 is a sectional view showing an optical arrangement at the distal end of the insertable portion of a conventional electronic endoscope.

In a conventional electronic endoscope, as illustrated in FIG. 11, light guides 46 are arranged, outside an imaging unit 45 constructed with the objective system comprising the objective lens system and the CCD, in parallel to the imaging unit 45. In such an electronic endoscope, two illumination systems are placed, but each of their diameters is smaller than that of the objective lens system and thus an illumination field is not very wide. Even though the imaging unit 45 has a wide-angle objective lens system, it is impossible to completely exert the performance of the imaging unit 45 because the illumination field of the illumination systems is narrow.

Thus, the electronic endoscope of the fourth embodiment uses the objective system of small diameter comprising the objective lens system 10 and the CCD 2, shown in the second embodiment, to construct the imaging unit. In the objective lens system 10 of the second embodiment, as mentioned previously, the second and third lens units 12 and 13 are arranged close to the stop 15, and hence the diameter of each of lenses constituting these lens units can be diminished.

Figure 12:
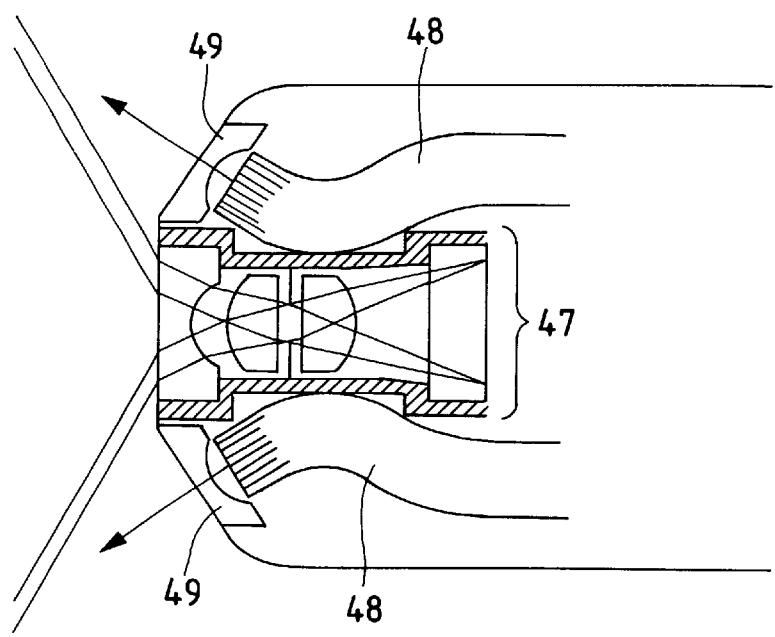
FIG. 12 is a sectional view showing an optical arrangement at the distal end of the insertable portion of the electronic endoscope of a fourth embodiment in the present invention.

Referring to FIG. 12, the electronic endoscope of the fourth embodiment, which uses the objective system of the second embodiment to construct an imaging unit 47, is such that the middle portion of the imaging unit 47 can be shaped into a fine, waisted cylindrical form. Consequently, when two light guides 48 are arranged in such a way that they are bent into convex shapes toward the imaging unit 47 and thereby are made to fall into this waisted portion along the periphery of the imaging unit 47, the exit surfaces of the light guides 48 are naturally directed outwardly (as indicated by arrows in the figure) at the distal end of the insertable section. Therefore, if illumination lenses 49 are placed immediately before the exit surfaces of the light guides 48 and exit windows are provided, a wider range of illumination field than in the conventional endoscope can be formed. In this way, an observable field of the wide-angle objective lens system 10 can easily be made to coincide with the illumination field of the illumination systems, and thus the electronic endoscope having a wide observation field can be provided.

Since the imaging unit 47 has the objective lens system 10 which is small in diameter, the diameter of the insertable section does not become large compared with that of the conventional endoscope even when the light guides 48 are arranged in bent shape.

Furthermore, the electronic endoscope of the fourth embodiment has the advantage that the insertion of the endoscope is facilitated because the exit surfaces of the illumination systems are directed outwardly and thus the distal end of the insertable section of the endoscope can be shaped into a streamline form, like a crest, in which the entrance surface of the objective lens system 10 is located at the headmost point.

Fifth Embodiment

Figure 13A:
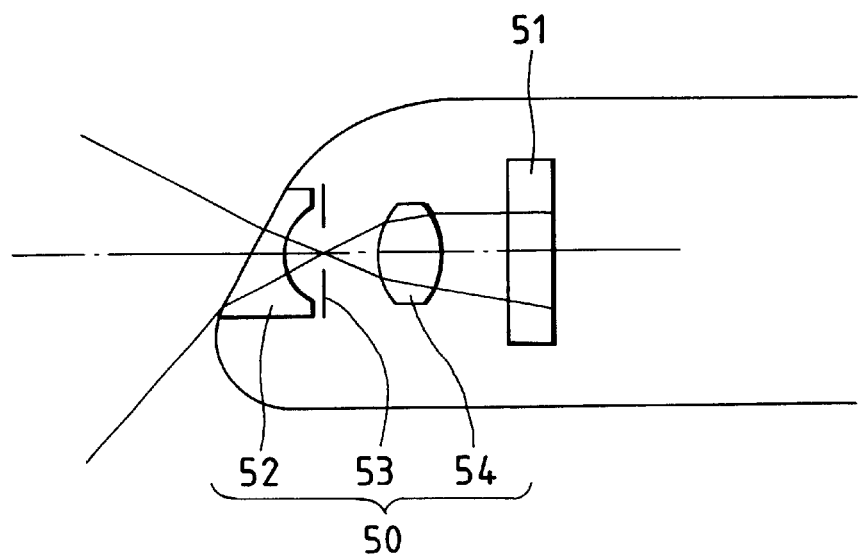
FIG. 13A is a sectional view showing an optical arrangement at the distal end of the insertable section of the electronic endoscope of a fifth embodiment in the present invention.
Figure 13B:
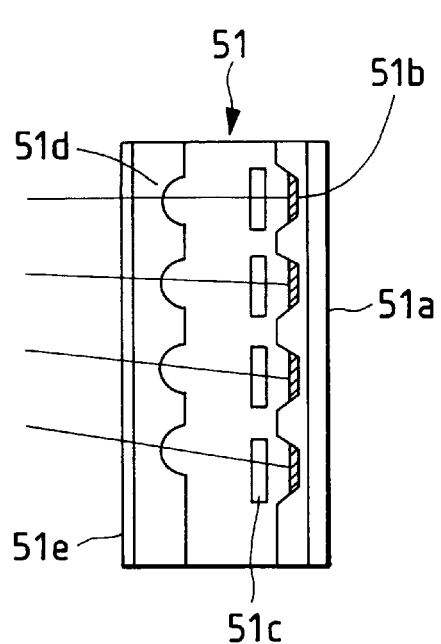
FIGS. 13B and 13C are sectional and front views, respectively, showing the configuration of a CCD in FIG. 13A.

In FIG. 13A, the electronic endoscope of this embodiment has, in order from the object side, an objective lens system 50 and a CCD 51 which are arranged apt the distal end thereof. The objective lens system 50 includes, in order from the object side, a first lens unit 52 of a negative lens, an aperture stop 53, and a second lens unit 54 of a positive lens. The first lens unit 52 constituting the objective lens system 50 is constructed so that the first surface thereof is inclined and decentered and the headmost end is pointed in order to shape the distal end of the insertable section of the endoscope into a round streamline form. Hence, a chief ray emerging from the objective lens system 50 and directed toward the uppermost portion of the CCD 51 shown in the figure is incident almost perpendicularly on the CCD 51, but a chief ray directed toward a lower portion is incident obliquely. Moreover, as the position of incidence of the chief ray on the CCD 51 is shifted downwardly, the angle of incidence of the ray increases progressively. Consequently, shading is liable to occur in going to the lower portion of the CCD.

Figure 13C:
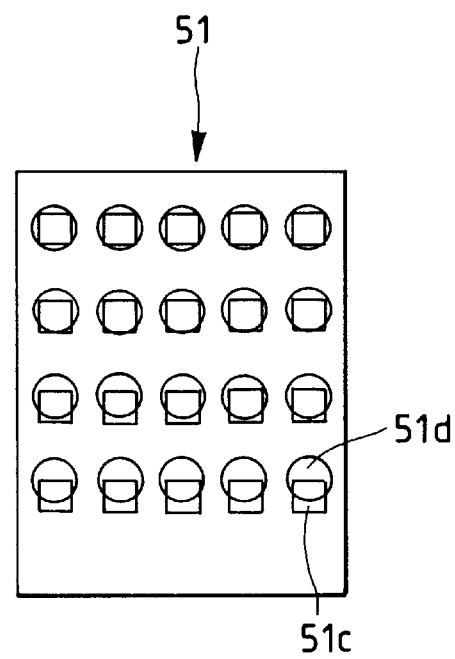

The CCD 51 used in the electronic endoscope of the fifth embodiment is thus designed so that, in going from the uppermost portion to the lower portion, the positions of microlenses arranged opposite to color filters and photosensors are progressively shifted upwardly. As illustrated in FIGS. 113B and 13C, the CCD 51, like the CCD 2 shown in the first embodiment, is constructed by laminating, in order, a photosensor section comprising photosensors 51*b* arranged on a substrate 51*a*, a color filter section comprising color filters 51*c* arranged, a microlens section comprising microlenses 51*d* arranged opposite to the photosensors 51*b* and the color filters 51*c*, and a glass cover 51*e*. Since, however, the CCD 51 is used together with the objective lens system 50 possessing the properties mentioned above, the optical axes of the microlenses 51*d* arranged in the uppermost portion of the CCD 51 coincide respectively with the centers of the color filter 51*c* and the photosensors 51*b* arranged opposite to the microlenses 51*d*. In going from the uppermost portion of the CCD 51 to the lower portion thereof, a shift between the center of each color filter 51*c* and photosensor 51*b* and the optical axis of each microlens 51*d* placed opposite thereto is progressively increased upwardly.

In the fifth embodiment, the arrangement of the microlenses 51*d* of the CCD 51 is made as in the foregoing, thereby obviating the production of shading.

In the electronic endoscope of the fifth embodiment, as mentioned above, the decentered lens is used to construct the objective lens system 50 so that the distal end of the insertable portion is shaped into the streamline form, and the CCD 51 possessing the properties described above is used together. As such, there is no fear that shading is produced, and a good image can be obtained by the electronic endoscope.

Sixth Embodiment

Figure 14A:
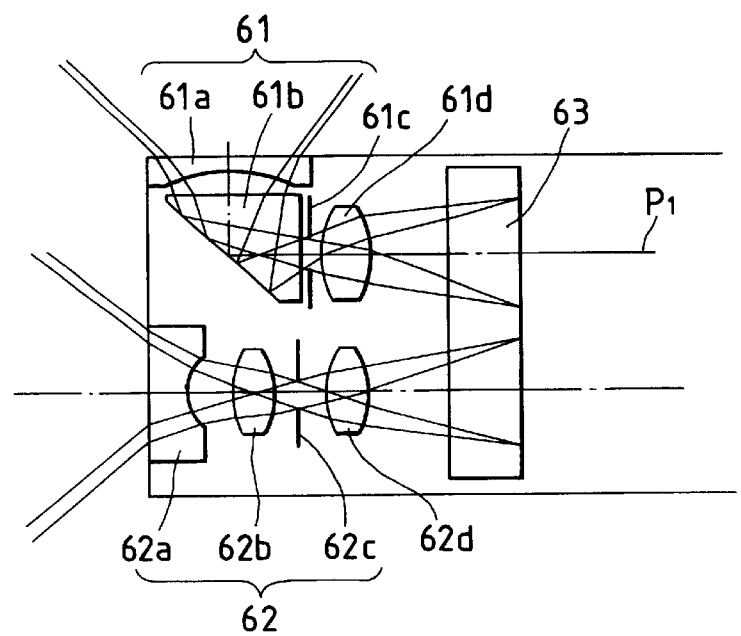
FIG. 14A is a sectional view showing an optical arrangement at the distal end of the insertable section of the electronic endoscope of a sixth embodiment in the present invention.

The objective system of the electronic endoscope of this embodiment, as shown in FIG. 14*a*, is constructed with an objective lens system 61 for side view, an objective lens system 62 for direct view, and a CCD 63. The objective lens system 61 for side view includes, in order from the object side, a first lens unit 61*a* of a negative lens, a prism 61*b* for deflecting a light beam emerging from the first lens unit 61*a* an aperture stop 61*c*, and a second lens unit 61*d* of a positive lens. Since the prism 61*b* and the second lens unit 61*d* have the aperture stop 61*c* between them and are arranged close thereto, the exit surface of the prism 61*b* and the lens diameter of the second lens unit 61*d* can be diminished, and at the same time, the entire length of the objective lens system 61 can be reduced. The objective lens system 61 is corrected for distortion in such a way that a chief ray directed toward the maximum image height is inclined outwardly with respect to the optical axis.

On the other hand, the objective lens system 62 includes, in order from the object side, a first lens unit 62*a* of a negative lens, a second lens unit 62*b* of a positive lens, an aperture stop 62*c*, and a third lens unit 62*d* of a positive lens. The objective lens unit 62, like that shown in the second embodiment, is such that the second lens unit 62*b* and the third lens unit 62*d* have the aperture stop 62*c* between them and are arranged close thereto. Hence, both the second and third lens units 62*b* and 62*d* can be made small in lens diameter, and the entire length of the objective lens system 62 can also be reduced. The objective lens system 62 is corrected for distortion in such a way that a chief ray directed toward the maximum image height is inclined outwardly with respect to the optical axis.

As discussed above, the objective lens system 62 for direct view, as well as the objective lens system 61 for side view, is constructed with lenses of small diameters, and thus, even when two kinds of objective lens systems are juxtaposed in the rigid portion at the distal end of the endoscope, the diameter of the insertable section of the endoscope will not be enlarged. In addition, since the entire length of the objective lens system is reduced, the length of the rigid portion at, the distal end of the endoscope can also be reduced.

Figure 14B:
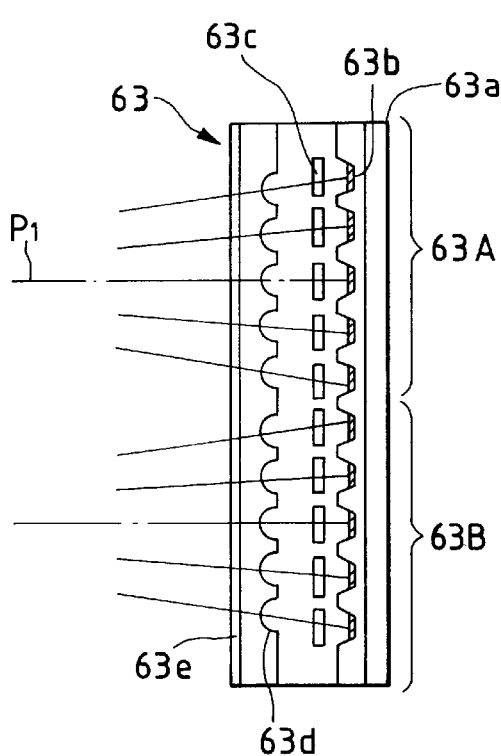
FIGS. 14B and 14C are sectional and front views, respectively, showing the configuration of a CCD in FIG. 14A.
Figure 14C:
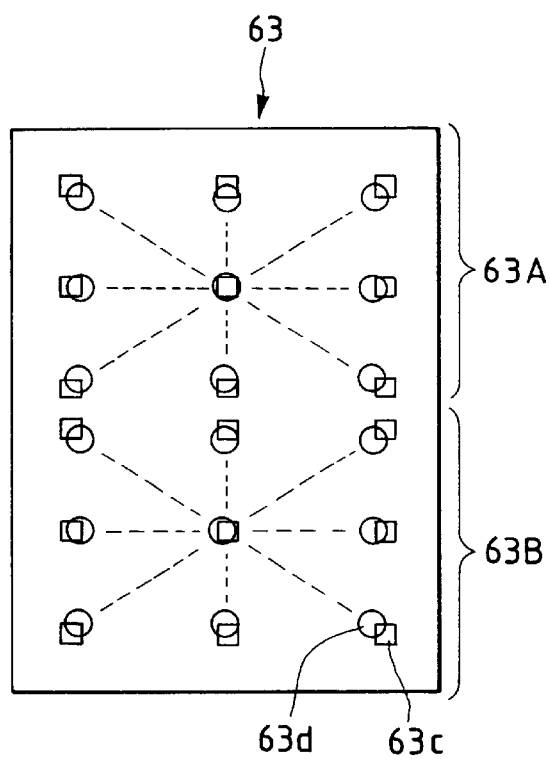

In the electronic endoscope of the sixth embodiment, an image formed by the objective lens system 61 for side view is different from that formed by the objective lens system 62 for direct view in the imaging position of the CCD 63. Therefore, the CCD 63, as illustrated in FIGS. 14B and 14C, is constructed with two regions, one, a region 63A, in which the image is formed by the objective lens system 61, and the other, a region 63B, in which the image is formed by the objective lens system 62.

Subsequently, a description is given of the constructions of the regions 63A and 63B of the CCD 63. Since the region 63A is the same as the region 63B, the construction of only the region 63A is explained here. The region 63A is constructed by laminating, in order, a photosensor section comprising photosensors 63b arranged in longitudinal and lateral directions on a substrate 63a, as a center at the photosensor 63b placed on an optical axis $P_1$ of the objective lens system 61; a color filter section comprising color filters 63c arranged in longitudinal and lateral directions, opposite to the photosensors 63b; a microlens section comprising microlenses 63d arranged in the same way, opposite to the photosensors 63b and the color filters 63c; and a glass cover 63e.

Here, the microlens placed on the optical axis $P_1$ of the objective lens system 61 is such that the optical axis of the microlens coincides with the optical axis $P_1$ of the objective lens system 61. Moreover, the optical axis of the microlens coincides with the center of the color filter and photosensor placed opposite to the microlens. For the entrance surface of the CCD 63, in separating from the $P_1$ of the objective lens system 61, a shift between the optical axis of each microlens and the center of each color filter and photosensor arranged opposite thereto is progressively increased toward the optical axis $P_1$ of the objective lens system 61.

By doing so, a light beam from the objective lens system 61 is rendered surely incident on each photosensor at which it is naturally expected to arrive, and shading is obviated.

An arrangement is also made so that as the microlens is located far off the optical axis $P_1$ of the objective lens system 61, its diameter increases progressively. Furthermore, as the microlens is located far off the optical axis, the radius of curvature of the lens surface is diminished and the lens power is strengthened. By doing so, provision is made so that the light-condensing performance of the microlens is improved progressively in going from the optical axis of the objective lens system 61 to the periphery of the region 63A. Consequently, the light beam reaching the periphery of the region 63A can be rendered incident on each photosensor without vignetting, and the luminance shading can be prevented from occurring.

In the electronic endoscope of the sixth embodiment, as mentioned above, the objective system disposed in the rigid portion at the distal end has two kinds of objective lens systems for side view and direct view, and thus the extension of the observation field can be intended. In addition, these two kinds of objective lens systems are each so small in size that even when they are arranged in parallel, the diameter of the insertable section of the endoscope will not be enlarged. By the two kinds of objective lens systems, distortion can be favorably corrected, and the CCD on which the images of the objective lens systems are formed will not give rise to shading.

Seventh Embodiment

As shown in FIG. 15, the distal end of the insertable section of the endoscope of thus embodiment includes an imaging unit 71 having an objective lens system for inclining a chief ray directed toward the maximum image height outwardly with respect to the optical axis and a CCD. Two light guides 72 are arranged parallel to the imaging unit 71. On the exit side of the light guides 72, illumination lenses 73 are placed.

In the electronic endoscope of the seventh embodiment, as mentioned above, illumination systems are arranged in such a way as to sandwich the imaging unit 71 between them. Consequently, illumination light emerging from the light guides 72 through the illumination lenses 73 is bright at or near the center of the observable field of the imaging unlit 71 and becomes darker in separating from the center.

This situation is shown in the graph of FIG. 16A. For this reason, even in the case of light reaching the CCD of the imaging unit 71, observation light from a periphery Q of the observation field becomes darker than that from a center C thereof. The position of incidence of the observation light on the CCD is such that the light from the center C of the observation field is incident on the center of the CCD, while that from the periphery Q is incident on the periphery thereof. In this case, where the photosensor section of the CCD has a uniform sensitivity, an available image also is darker on its periphery than at its center, and is difficult to observe.

Here, in the case where the light-distribution characteristics of the illumination systems are as shown in the graph of FIG. 16A, if the sensitivity distribution of the photosensor section of the CCD is set as shown in the graph of FIG. 16B, an image derived from the electronic endoscope, as depicted in the graph of FIG. 16C, should have even brightness as a whole.

Figure 17:
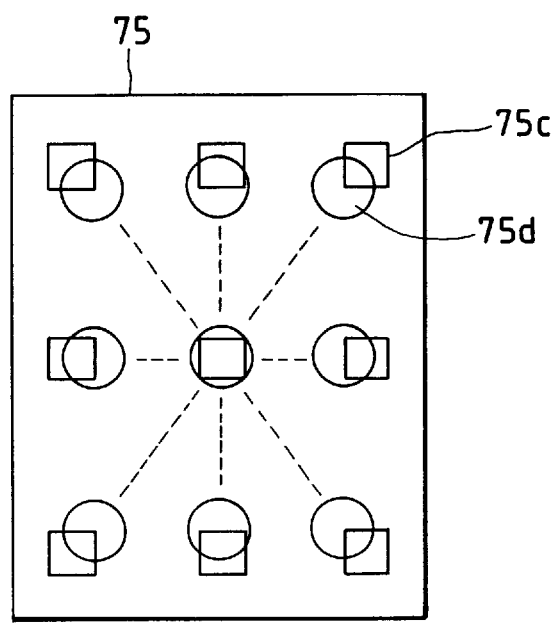
FIG. 17 is a front view showing the configuration of a CCD of FIG. 15.

Thus, the seventh embodiment uses a CCD 75 such as that shown in FIG. 17. The CCD 75 is constructed by laminating, in order, a photosensor section comprising photosensors arranged longitudinally and laterally on a substrate, as a center at a photosensor placed on the optical axis of the objective lens system; a color filter section comprising color filters 75c arranged longitudinally and laterally, opposite to the photosensors; a microlens section comprising microlenses 75d arranged in the same way, opposite to the photosensors and the color filters 75c; and a glass cover.

Here, the microlens 75d for introducing light into the photosensor placed on the optical axis of the objective lens system is situated immediately before the color filter 75c located opposite to the photosensor (namely, the optical axis of the microlens 75d is made to coincide with the center of the color filter 75c and photosensor). An arrangement is made so that, in separating from the optical axis of the objective lens system, the microlens 75d for introducing light into the photosensor is situated closer to the optical axis than the color filter 75c located opposite to the photosensor (namely, in separating from the optical axis of the objective lens system, the position of the optical axis of the microlens 75d is increasingly shifted from the center of the color filter 75c and photosensor toward the optical axis of the objective lens system).

Furthermore, in keeping with the light-distribution characteristics of the illumination systems, the sensitivity of each photosensor is increased progressively in going from the middle of the CCD to the periphery thereof. The image of uniform brightness is thus obtained over the entire CCD.

By such an arrangement, the electronic endoscope of the seventh embodiment is capable of preventing the production of shading and obtaining the observation image with uniform brightness in view of the light-distribution characteristics of the illumination systems.

Each microlens of the CCD may be designed so that its curvature reduces progressively in going from the middle to the periphery. Alternatively, only microlenses arranged near the middle may be eliminated. By doing so, the brightness of the image obtained by the electronic endoscope can be made uniform. Moreover, in keeping with the light-distribution characteristics of the illumination systems, even when the microlenses arranged on the periphery of the CCD are made larger in diameter or numerical aperture, or smaller in F-number than the microlenses at the middle, the amount of condensed light for the photosensors located on the periphery is raised and light-condensing performance cain be improved, so that the same effect is secured.

Eighth Embodiment

Figure 18:
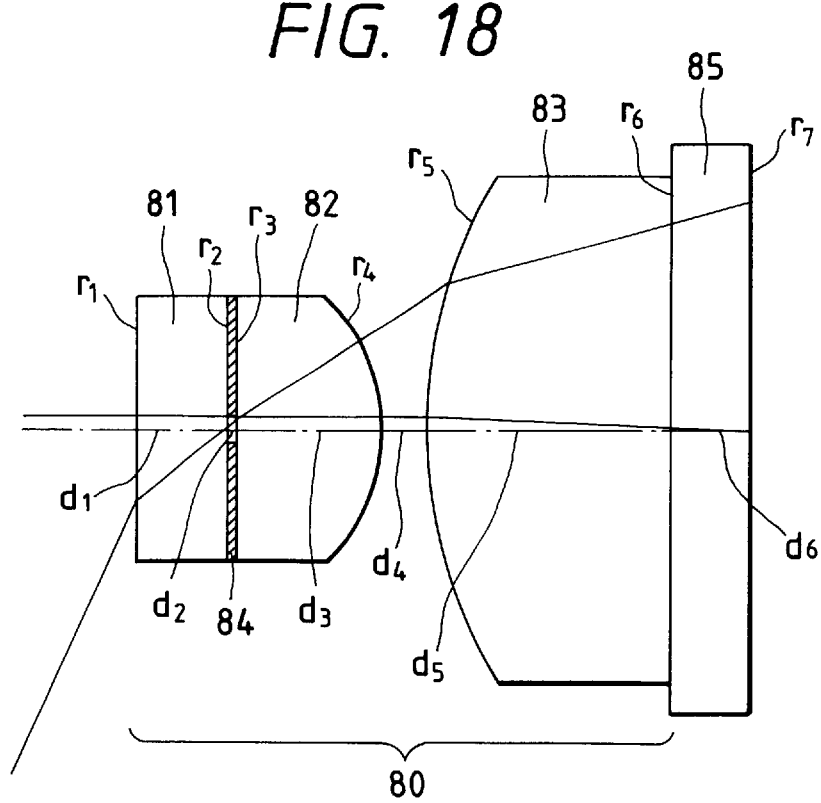
FIG. 18 is a sectional view showing the arrangement, developed along the optical axis, of an objective system placed in a rigid portion at the distal end of the insertable section of the electronic endoscope of an eighth embodiment in the present invention.

In FIG. 18, an objective lens system 80 of the electronic endoscope of this embodiment includes, in order from the object side, a plane-parallel glass cover 81, a first lens unit 82 of a positive lens, and a second lens unit 83 of a positive lens. An aperture stop 84 is provided on the exit surface of the glass cover 81. The second lens unit 83 is made of material absorbing infrared light. The second lens unit 83 is cemented to a CCD glass cover 85 in such a way that its optical axis is aligned with the center of the imaging area of the CCD. The package of the CCD, because of its rectangular form, is difficult to fix, but it is fixed by setting the second lens unit 83 in a frame whose inside is circular, with the CCD fixed to the second lens unit 83 which is circular.

In FIG. 19A, the Conventional objective system has been designed so that the outside diameter of a lens 83' or plane-parallel plate which is cemented to the CCD glass cover is considerably large for the maximum image height. Specifically, in the example of this figure, the objective lens system is telecentric, and thus when an attempt is made so that off-axis chief rays on the upper side are not eclipsed, the outside diameter of the lens cemented to the CCD glass cover must be enlarged. As a result, the outside diameter of the frame also becomes large and the outside diameter of the distal end of the endoscope is rendered large accordingly.

In FIG. 19B, since the objective system of the present invention is such that the off-axis chief rays are inclined, the outside diameter of the lens 83 cemented to the CCD glass cover can be diminished. Hence, the outside diameter of the frame can also be diminished. When the outside diameter of a lens or plane-parallel plate to be cemented is denoted by $\phi$ and the maximum image height is denoted by IH, the objective lens system of the present invention is constructed so that $$\phi/2 < 1.2 \times IH \quad (3)$$

and preferably $$\phi/2 < 1.1 \times IH \quad (4)$$

In the present invention, it is desirable that an angle of inclination θ of the chief ray incident on the CCD, that is, on the image plane is about 10–30°. If the angle is smaller than 10°, the outside diameter of a lens situated close to the image plane (the second lens unit in this case) will be enlarged, and consequently, the outside diameter of the distal end of the endoscope becomes large, which is unfavorable. Conversely, if it is larger than 30°, the prevention of shading becomes incomplete, which is unfavorable.

As shown in FIG. 20, in order to set the angle of inclination θ at about 10–30°, it is desirable to satisfy the following condition:

$$1.5 < L/f < 4 \quad (5)$$

where L is an equivalent air length from the exit pupil O to an image plane S and f is a focal length.

If L/f is less than 1.5, the angle θ will be excessively increased, while it is larger than 4, the angle θ will be too small. Where the objective lens system includes as few as three lenses or even a smaller number of lenses, it is desirable to satisfy the following relation in view of correction for aberration:

$$L'/f < 1.5 \quad (6)$$

where L' is an equivalent air length from the exit pupil O to the aperture stop 84.

If L'/f is larger than 1.5, aberration produced close to the image will be particularly deteriorated, which is unfavorable.

The following is numerical data of individual optical members constituting the objective lens system 80 used in the electronic endoscope of the eighth embodiment.

f = 1.477, F-number = 7.8, Image height = 1.533, Angle of view = 133°

$r_1 = \infty$
  $d_1 = 0.6000$  $n_1 = 1.51633$  $v_1 = 64.14$
$r_2 = \infty$ (the aperture stop 84)
  $d_2 = 0.0300$
$r_3 = \infty$
  $d_3 = 0.9633$  $n_3 = 1.72916$  $v_3 = 54.68$
$r_4 = -1.3173$
  $d_4 = 0.2891$
$r_5 = 3.5010$
  $d_5 = 1.6000$  $n_5 = 1.51400$  $v_5 = 75.00$
$r_6 = \infty$
  $d_6 = 0.5000$  $n_6 = 1.49700$  $v_6 = 81.54$
$r_7 = \infty$ L/f = 1.887, L'/f = 0.352

Ninth Embodiment

Figure 21:
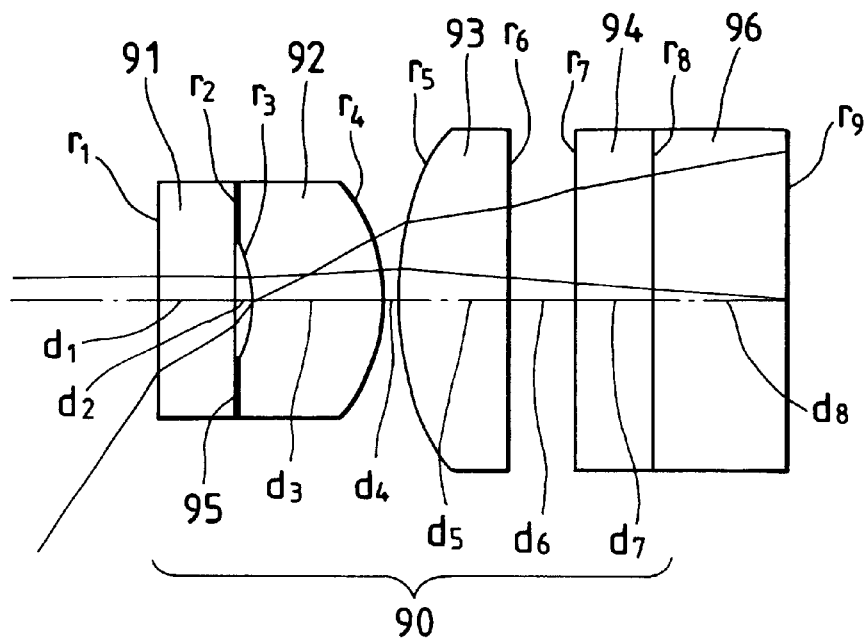
FIG. 21 is a sectional view showing the arrangement, developed along the optical axis, of an objective system placed in a rigid portion at the distal end of the insertable section of the electronic endoscope of a ninth embodiment in the present invention.

In this embodiment, as shown in FIG. 21, an objective lens system 90 of the electronic endoscope includes, in order from the object side, a plane-parallel glass cover 91, a first lens unit 92 of a positive lens, a second lens unit 93 of a positive lens, and a plane-parallel infrared absorbing filter 94. An aperture stop 95 is provided on the entrance surface of the first lens unit 92. The infrared absorbing filter 94 is cemented to a CCD glass cover 96.

The following is numerical data of individual optical members constituting the objective lens system 90 used in the electronic endoscope of the ninth embodiment.

f = 0.991, F-number = 4.0, Image height = 0.8, Angle of view = 113°

$r_1 = \infty$
  $d_1 = 0.4000$  $n_1 = 1.51633$  $v_1 = 64.14$
$r_2 = \infty$ (the aperture stop 95)
  $d_2 = 0.0800$
$r_3 = -1.0297$
  $d_3 = 0.6803$  $n_3 = 1.88300$  $v_3 = 40.76$
$r_4 = -0.9766$
  $d_4 = 0.0678$
$r_5 = 1.6673$
  $d_5 = 0.5674$  $n_5 = 1.88300$  $v_5 = 40.76$
$r_6 = \infty$
  $d_6 = 0.3256$
$r_7 = \infty$
  $d_7 = 0.4000$  $n_7 = 1.51400$  $v_7 = 75.00$
$r_8 = \infty$
  $d_8 = 0.7000$  $n_8 = 1.51633$  $v_8 = 64.14$
$r_9 = \infty$ L/f = 2.266, L'/f = 0.467

Tenth Embodiment

Figure 22:
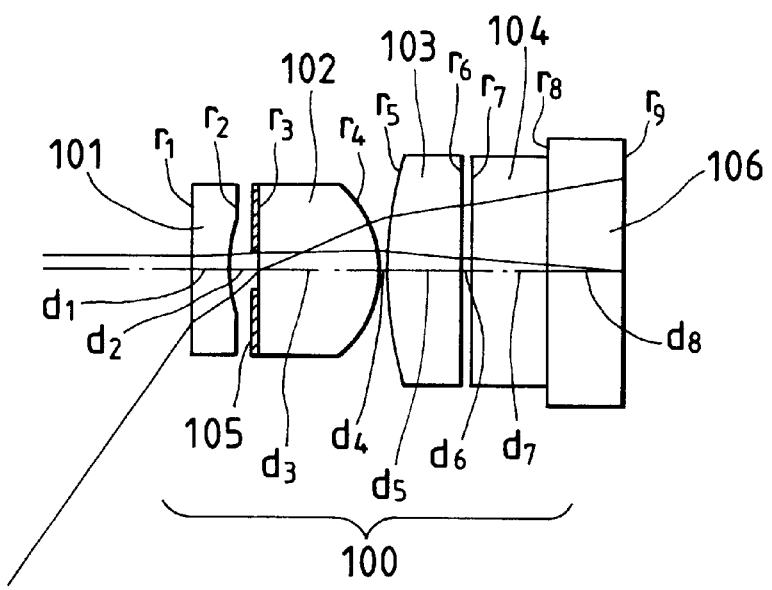
FIG. 22 is a sectional view showing the arrangement, developed along the optical axis, of an objective system placed in a rigid portion at the distal end of the insertable section of the electronic endoscope of a tenth embodiment in the present invention.

In FIG. 22, an objective lens system 100 of the electronic endoscope of this embodiment includes, in order from the object side, a first lens unit 101 of a negative lens, a second lens unit 102 of a positive lens, a third lens unit 103 of a positive lens, and a plane-parallel infrared absorbing filter 104. An aperture stop 105 is provided on the entrance surface of the second lens unit 102. The infrared absorbing filter 104 is cemented to a CCD cover glass 106.

The following is numerical data of individual optical members constituting the objective lens system 100 used in the electronic endoscope of the tenth embodiment.

f = 0.585, F-number = 4.0, Image height = 0.5, Angle of view = 113°

$r_1 = \infty$
$\quad d_1 = 0.2000 \quad n_1 = 1.51633 \quad \nu_1 = 64.14$
$r_2 = 0.9068$
$\quad d_2 = 0.1392$
$r_3 = \infty$ (the aperture stop 105)
$\quad d_3 = 0.6105 \quad n_3 = 1.88300 \quad \nu_3 = 40.76$
$r_4 = -0.6105$
$\quad d_4 = 0.0500$
$r_5 = 2.3470$
$\quad d_5 = 0.3780 \quad n_5 = 1.88300 \quad \nu_5 = 40.76$
$r_6 = \infty$
$\quad d_6 = 0.0300$
$r_7 = \infty$
$\quad d_7 = 0.4000 \quad n_7 = 1.51400 \quad \nu_7 = 75.00$
$r_8 = \infty$
$\quad d_8 = 0.4000 \quad n_8 = 1.51633 \quad \nu_8 = 64.14$
$r_9 = \infty$ L/f = 2.8, L'/f = 0.863

Eleventh Embodiment

Figure 23:
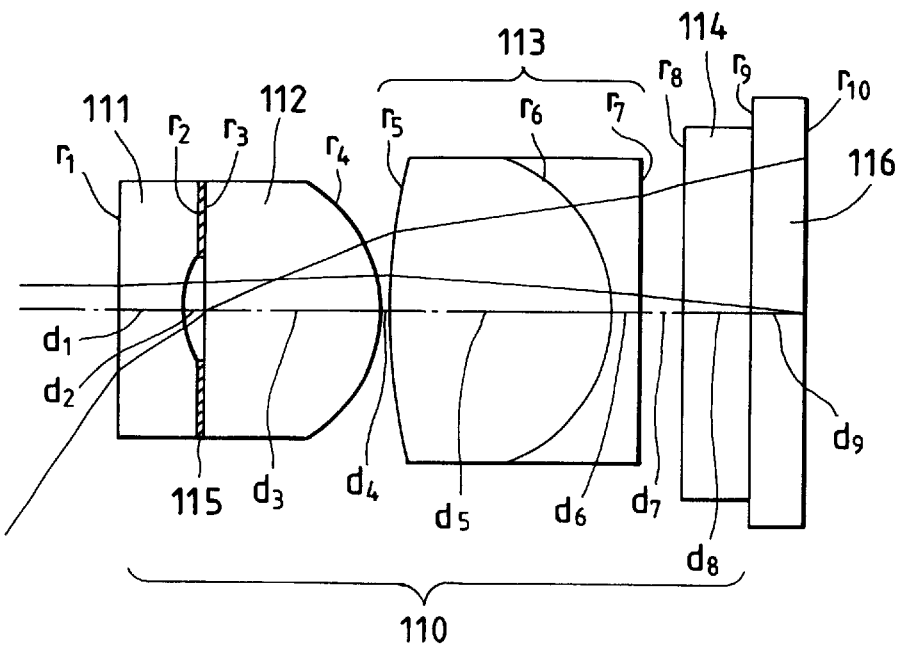
FIG. 23 is a sectional view showing the arrangement, developed along the optical axis, of an objective system placed in a rigid portion at the distal end of the insertable section of the electronic endoscope of an eleventh embodiment in the present invention.

In this embodiment, as shown in FIG. 23, an objective lens system 110 of the electronic endoscope includes, in order from the object side, a first lens unit 111 of a negative lens, a second lens unit 112 of a positive lens, a third lens unit 113 of a positive lens, and a plane-parallel infrared absorbing filter 114. An aperture stop 115 is provided on the entrance surface of the second lens unit 112. The infrared absorbing filter 114 is cemented to a CCD glass cover 116. The third lens unit 113 is a cemented lens composed of a positive lens and a negative lens. In this case, the interface of the cemented lens with the convex surface directed toward the image side brings about the condition that is concentric with respect to the aperture stop, and this is favorable for correction of aberration. Moreover, even from the point of view that the thickness of an edge portion of the positive lens is secured, it is desirable that the interface is convex toward the image side.

The following is numerical data of individual optical members constituting the objective lens system 110 used in the electronic endoscope of the eleventh embodiment.

f = 1.371, F-number = 3.7, Image height = 1.2, Angle of view = 113°

$r_1 = \infty$
$\quad d_1 = 0.5000 \quad n_1 = 1.51633 \quad \nu_1 = 64.14$
$r_2 = 1.0425$
$\quad d_2 = 0.1200$
$r_3 = \infty$ (the aperture stop 115)
$\quad d_3 = 1.3606 \quad n_3 = 1.88300 \quad \nu_3 = 40.76$
$r_4 = -1.1686$
$\quad d_4 = 0.0500$
$r_5 = 5.5829$
$\quad d_5 = 1.6832 \quad n_5 = 1.77250 \quad \nu_5 = 49.60$
$r_6 = -1.2720$
$\quad d_6 = 0.2000 \quad n_6 = 1.84666 \quad \nu_6 = 23.78$
$r_7 = \infty$
$\quad d_7 = 0.3279$
$r_8 = \infty$
$\quad d_8 = 0.5000 \quad n_8 = 1.51400 \quad \nu_8 = 64.14$
$r_9 = \infty$
$\quad d_9 = 0.4000 \quad n_9 = 1.51633 \quad \nu_9 = 64.15$
$r_{10} = \infty$ L/f = 2.653, L'/f = 0.646

Twelfth Embodiment

Figure 24:
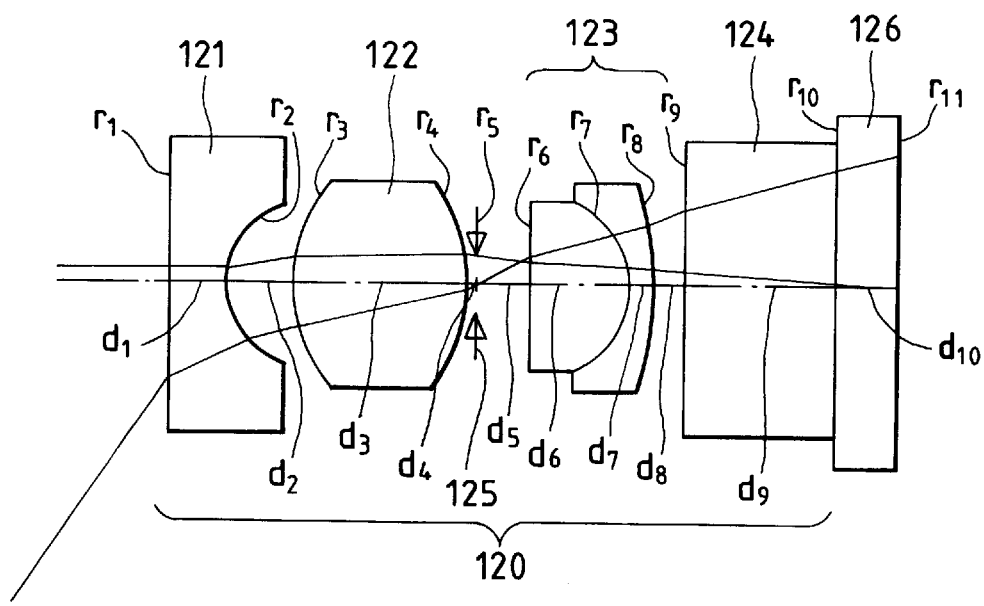
FIG. 24 is a sectional view showing the arrangement, developed along the optical axis, of an objective system placed in a rigid portion at the distal end of the insertable section of the electronic endoscope of a twelfth embodiment in the present invention.

As shown in FIG. 24, an objective lens system 120 of the electronic endoscope of this embodiment is constructed with, in order from the object side, a first lens unit 121 of a negative lens, second lens unit 122 of a positive lens, a third lens unit 123 of a positive lens, and a pane-parallel infrared absorbing filter 124. An aperture stop 125 is interposed between the second lens unit 122 and the third lens unit 123. The infrared absorbing filter 124 is cemented to a CCD glass cover 126. The third lens unit 123 is a cemented lens composed of a negative lens and a positive lens.

The following is numerical data of individual optical members constituting the objective lens system 120 used in the electronic endoscope of the twelfth embodiment.

f = 0.99, F-number = 4.7, Image height = 0.925, Angle of view = 113°

$r_1 = \infty$
$\quad d_1 = 0.3800 \quad n_1 = 1.88300 \quad \nu_1 = 40.76$
$r_2 = 0.5995$
$\quad d_2 = 0.4354$
$r_3 = 1.2166$
$\quad d_3 = 1.1110 \quad n_3 = 1.88300 \quad \nu_3 = 40.76$
$r_4 = -1.3029$
$\quad d_4 = 0.0662$
$r_5 = \infty$ (the aperture stop 125)
$\quad d_5 = 0.3600$
$r_6 = -7.0966$
$\quad d_6 = 0.6392 \quad n_6 = 1.77250 \quad \nu_6 = 49.60$
$r_7 = -0.6360$
$\quad d_7 = 0.1487 \quad n_7 = 1.84666 \quad \nu_7 = 23.78$
$r_8 = -2.5814$
$\quad d_8 = 0.2133$
$r_9 = \infty$
$\quad d_9 = 1.0000 \quad n_9 = 1.51400 \quad \nu_9 = 75.00$
$r_{10} = \infty$
$\quad d_{10} = 0.4000 \quad n_{10} = 1.51633 \quad \nu_{10} = 64.14$
$r_{11} = \infty$ L/f = 2.125, L'/f = 0.167

Thirteenth Embodiments

Figure 25:
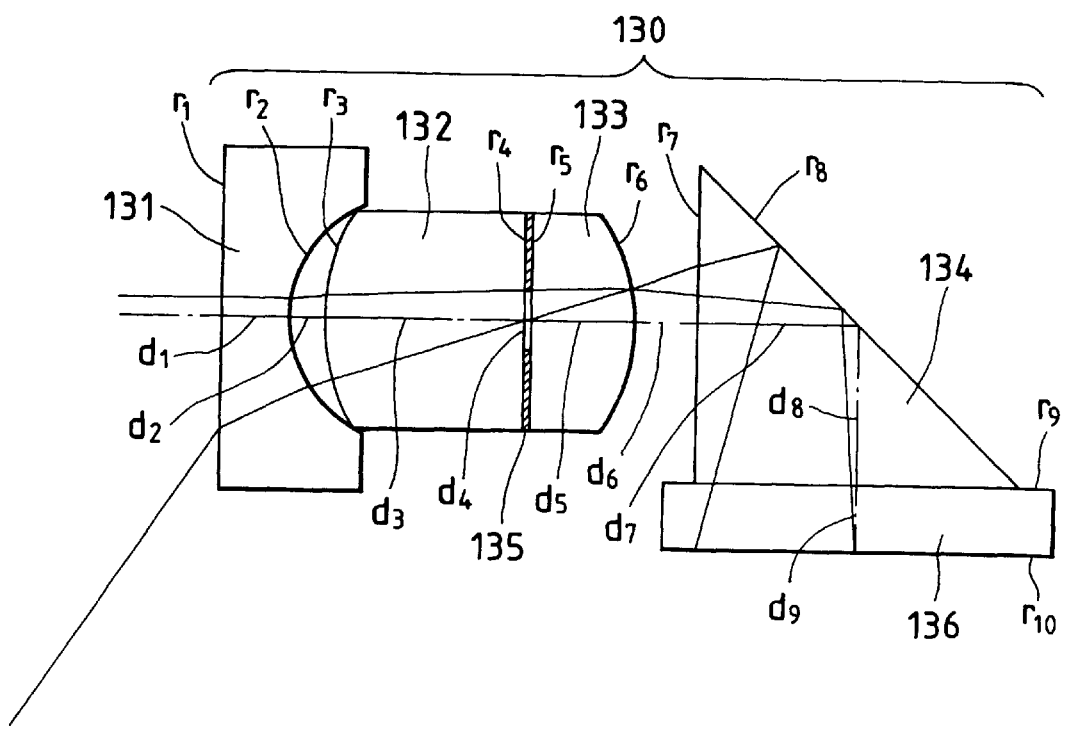
FIG. 25 is a sectional view showing the arrangement, developed along the optical axis, of an objective system placed in a rigid portion at the distal end of the insertable section of the electronic endoscope of a thirteenth embodiment in the present invention.

In FIG. 25, an objective lens system 130 of the electronic endoscope of this embodiment includes, in order from the object side, a first lens unit 131 of a negative lens, a second lens unit 132 of a positive lens, a third liens unit 133 of a positive lens, and a prism 134. An aperture stop 135 is interposed between the second lens unit 132 and the-third lens unit 133. The prism 134 is cemented to a CCD glass cover 136. The CCD is disposed in the longitudinal direction of the endoscope, and thereby downsizing of the diameter of the distal end is intended.

The following is numerical data of individual optical members constituting the objective lens system 130 used in the electronic endoscope of the thirteenth embodiment.

f = 1.288, F-number = 4.9, Image height = 1.2, Angle of view = 114°

$r_1 = \infty$
$\quad d_1 = 0.5000 \quad n_1 = 1.88300 \quad \nu_1 = 40.76$
$r_2 = 0.9218$
$\quad d_2 = 0.3000$
$r_3 = 1.7808$
$\quad d_3 = 1.4410 \quad n_3 = 1.84666 \quad \nu_3 = 23.78$
$r_4 = \infty$ (the aperture stop 135)
$\quad d_4 = 0.0300$
$r_5 = \infty$
$\quad d_5 = 0.7939 \quad n_5 = 1.88300 \quad \nu_5 = 40.76$
$r_5 = -1.3483$
$\quad d_6 = 0.4295$
$r_7 = \infty$
$\quad d_7 = 1.2000 \quad n_7 = 1.51633 \quad \nu_7 = 64.14$
$r_8 = \infty$ (the reflecting surface)

-continued

| | $d_8 = 1.2000$ | $n_8 = 1.51633$ | $v_8 = 64.14$ |
|---|---|---|---|
| $r_9 = \infty$ | | | |
| | $d_9 = 0.5000$ | $n_9 = 1.51633$ | $v_9 = 64.14$ |
| $r_{10} = \infty$ | | | |

L/f = 2.316, L'/f = 0.147

Fourteenth Embodiment

Figure 26:
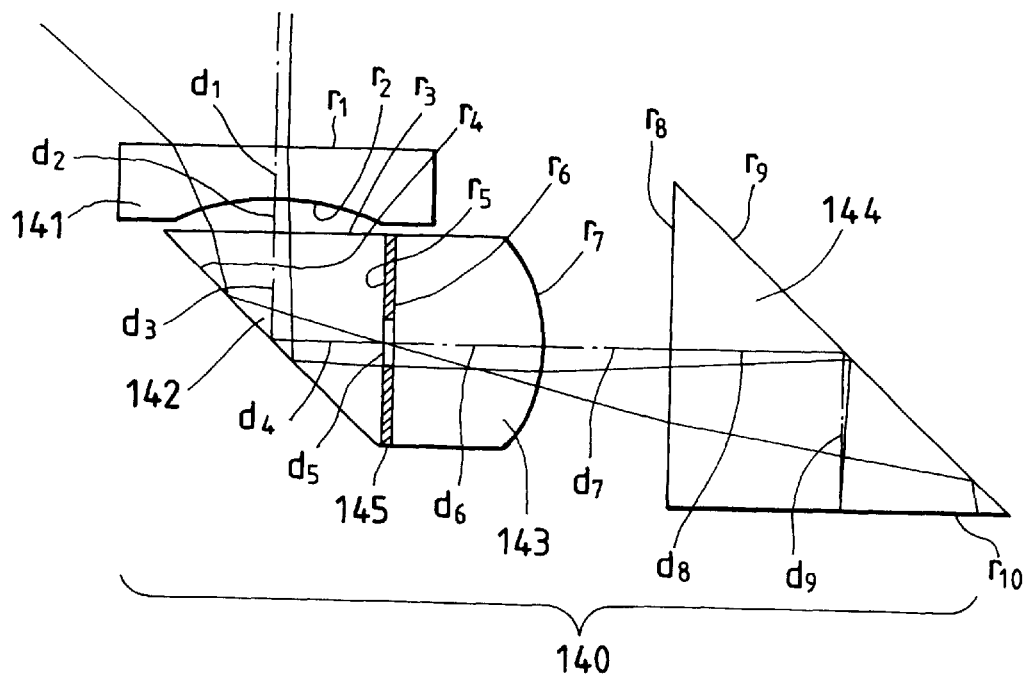
FIG. 26 is a sectional view showing the arrangement, developed along the optical axis, of an objective lens system placed in a rigid portion at the distal end of the insertable section of the electronic endoscope of a fourteenth embodiment in the present invention.

In FIG. 26, an objective lens system 140 of the electronic endoscope of this embodiment includes, in order from the object side, a first lens unit 141 of a negative lens, a first prism 142, a second lens unit 143 of a positive lens, and a second prism 144. An aperture stop 145 is interposed between the first prism 142 and the second lens unit 143. This electronic endoscope is an endoscope for side view with which the visual field is observed, and thus the CCD is placed horizontally along the longitudinal direction of the endoscope to intend downsizing of the diameter. This downsizing is intended even by cementing the second prism 144 directly to the imaging surface of the CCD without using the glass cover.

The following is numerical data of individual optical members constituting the objective lens system 140 used in the electronic endoscope of the fourteenth embodiment.

f = 0.631, F-number = 6.5, Image height = 0.5, Angle of view = 96°

| $r_1 = \infty$ | | | |
|---|---|---|---|
| | $d_1 = 0.2000$ | $n_1 = 1.88300$ | $v_1 = 40.76$ |
| $r_2 = 0.8797$ | | | |
| | $d_2 = 0.1200$ | | |
| $r_3 = \infty$ | | | |
| | $d_3 = 0.4000$ | $n_3 = 1.80610$ | $v_3 = 40.92$ |
| $r_4 = \infty$ (the reflecting surface) | | | |
| | $d_4 = 0.4000$ | $n_4 = 1.80610$ | $v_4 = 40.92$ |
| $r_5 = \infty$ (the aperture stop 145) | | | |
| | $d_5 = 0.0300$ | | |
| $r_6 = \infty$ | | | |
| | $d_6 = 0.5289$ | $n_6 = 1.90135$ | $v_6 = 31.55$ |
| $r_7 = -0.6525$ | | | |
| | $d_7 = 0.4545$ | | |
| $r_8 = \infty$ | | | |
| | $d_8 = 0.6000$ | $n_8 = 1.51633$ | $v_8 = 64.14$ |
| $r_9 = \infty$ (the reflecting surface) | | | |
| | $d_9 = 0.6000$ | $n_9 = 1.51633$ | $v_9 = 64.14$ |
| $r_{10} = \infty$ | | | |

L/f = 2.826, L'/f = 0.363

Fifteenth Embodiment

Figure 27:
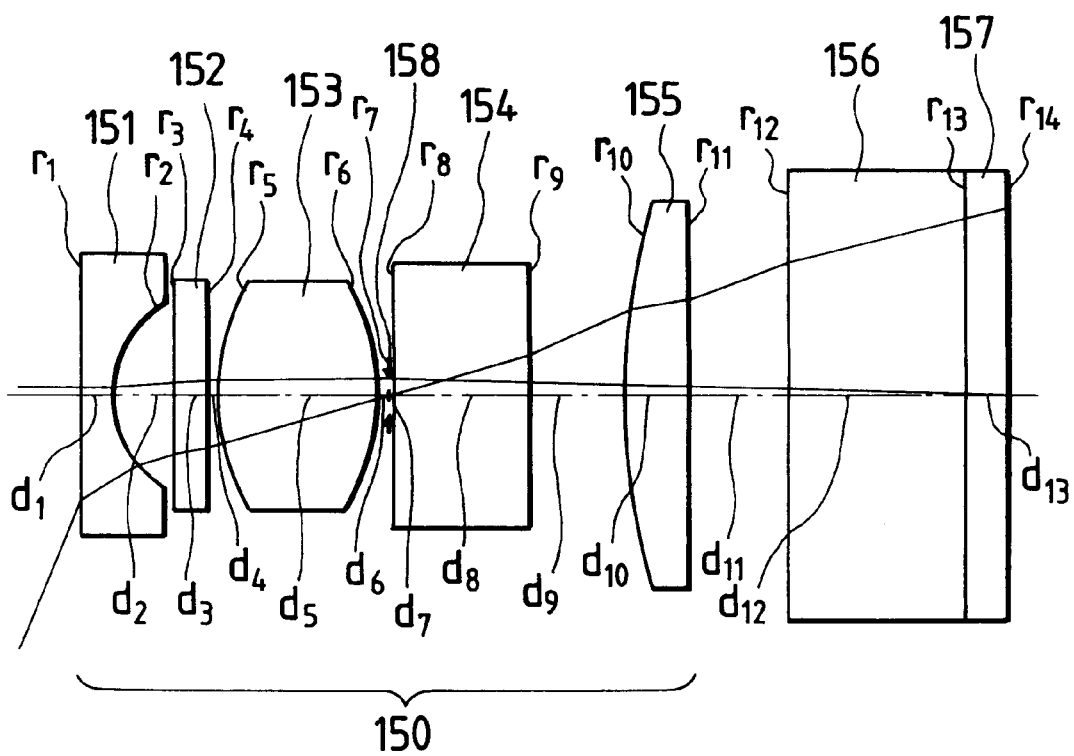
FIG. 27 is a sectional view showing the arrangement, developed along the optical axis, of an objective system placed in a rigid portion at the distal end of the insertable section of the electronic endoscope of a fifteenth embodiment in the present invention.

In FIG. 27, an objective lens system 150 of the electronic endoscope of this embodiment includes, in order from the object side, a first lens unit 151 of a negative lens, a plane-parallel filter 152 for cutting off wavelengths in a particular region, a second lens unit 153 of a positive lens, a plane-parallel filter 154 for cutting off wavelengths in a particular region, and a third lens unit 155 of a positive lens. A plane-parallel plate 156 and a plane-parallel plate 157 are glass covers. An aperture stop 158 is provided between the second lens unit 153 and the third lens unit 155. The first lens unit 151 is configured to be plano-concave, the second lens unit 153 to be biconvex, and the third lens unit 155 to be plano-convex. The filter 152 is a laser-light cutoff filter coated with an interference film on at least one side thereof, while the filter 154 is an infra-red cutoff filter of an absorption type. These filters 152 and 154 may be interposed between the first lens unit 151 and the second lens unit 153, between the second lens unit 153 and the third lens unit 155, or between the third lens unit 155 and the image plane. The absorption filter 154 may also be coated with the interference film on at least one side thereof. Moreover, it is possible that two filters, each having the interference film on at least one side thereof, are used. It is also possible that the interference film is provided on at least one side of any lens to bring about a filter function. Only one filter may be used in the objective lens system.

The following is numerical data of individual optical members constituting the objective lens system 150 used in the electronic endoscope of the fifteenth embodiment.

f = 2.11, F-number = 9.2, Image height = 2.12, Angle of view = 113.7°

| $r_1 = \infty$ | | | |
|---|---|---|---|
| | $d_1 = 0.4000$ | $n_1 = 1.88300$ | $v_1 = 40.76$ |
| $r_2 = 1.1481$ | | | |
| | $d_2 = 0.6586$ | | |
| $r_3 = \infty$ | | | |
| | $d_3 = 0.4000$ | $n_3 = 1.52287$ | $v_3 = 56.89$ |
| $r_4 = \infty$ | | | |
| | $d_4 = 0.1$ | | |
| $r_5 = 2.3332$ | | | |
| | $d_5 = 1.8557$ | $n_5 = 1.64769$ | $v_5 = 33.79$ |
| $r_6 = -2.3332$ | | | |
| | $d_6 = 0.1$ | | |
| $r_7 = \infty$ (the aperture stop 158) | | | |
| | $d_7 = 0.03$ | | |
| $r_8 = \infty$ | | | |
| | $d_8 = 1.60$ | $n_8 = 1.51400$ | $v_8 = 75.00$ |
| $r_9 = \infty$ | | | |
| | $d_9 = 1.0516$ | | |
| $r_{10} = 6.4837$ | | | |
| | $d_{10} = 0.7699$ | $n_{10} = 1.76163$ | $v_{10} = 53.81$ |
| $r_{11} = \infty$ | | | |
| | $d_{10} = 1.1661$ | | |
| $r_{12} = \infty$ | | | |
| | $d_{12} = 2.0000$ | $n_{12} = 1.51633$ | $v_{12} = 64.15$ |
| $r_{13} = \infty$ | | | |
| | $d_{13} = 0.5000$ | $n_{13} = 1.51633$ | $v_{13} = 64.15$ |
| $r_{14} = \infty$ | | | |

What is claimed is:

1. An electronic endoscope, comprising:
    an objective lens system which causes chief rays that are directed toward a maximum image height to be inclined outwardly with respect to an optical axis of said objective lens system; and
    a solid-state image sensor having a light-receiving surface on which a plurality of pixels are arrayed,
    wherein said solid-state image sensor is configured so that each of said plurality of pixels generates a largest power when alight beam is incident thereon with a predetermined outward inclination in reference to the optical axis, and said outward inclination of a light beam that causes the pixel to generate the largest power increases as a position of the pixel on said light-receiving surface separates from a center of said light-receiving surface at least in one direction.

2. An electronic endoscope, comprising:
    a plurality of objective lens systems, each of which causes chief rays directed toward a maximum image height to be inclined outwardly with respect to an optical axis thereof; and
    a solid-state image sensor having a single light-receiving surface on which a plurality of pixels are arrayed and which receives images formed by said plurality of objective lens systems,
    wherein said solid-state image sensor is configured so that each of said plurality of pixels generates a largest power when 1 light beam coming from one of said plurality of objective lens systems is incident thereon with a predetermined outward inclination in reference to the optical axis of the predetermined one of said plurality of objective lens systems, and the outward inclination of a light beam that causes the pixel to generate the largest power increases as a position of the pixel on said single light-receiving surface separates from a center of the image formed by the predetermined one of said plurality of objective lens systems.

3. An electronic endoscope, comprising:
an objective lens system;
a plurality of illumination optical systems possessing light-distribution characteristics such that illuminance on a periphery of a visual field of said objective lens system is lower than illuminance at a center thereof; and
a solid-state image sensor in which, when light of uniform intensity is incident on a light-receiving surface thereof, each of pixels located on a periphery of said light-receiving surface produces a higher power than each of pixels located at a middle thereof.

4. An electronic endoscope according to claim 1, wherein said objective lens system has an angle of view of at least 100°.

5. An electronic endoscope according to claim 1, wherein a maximum diameter of lens components constituting said objective lens system is smaller than a short side of said solid-state image sensor.

6. An electronic endoscope according to claim 1, wherein a vignetting factor of said objective lens system relative to a light beam directed toward the maximum image height is less than 1.

7. An electronic endoscope according to claim 1, wherein said objective lens system includes three or less lenses.

8. An electronic endoscope according to claim 1, wherein at least one reflecting prism is placed in an optical path from a front end of said objective lens system to said light-receiving surface of said solid-state image sensor, and said solid-state image sensor is placed horizontally along a longitudinal direction of an insertable section of said endoscope.

9. An electronic endoscope according to claim 8, wherein at least one of an entrance surface, an exit surface, and a reflecting surface of said reflecting prism is provided with an optical power.

10. An electronic endoscope according to claim 8, wherein an optical element having an optical power is cemented to one of an entrance surface and an exit surface of said reflecting prism.

11. An electronic endoscope according to claim 1, wherein a distal end of said endoscope is shaped into a crest-like form in which an entrance window of said objective lens system is located at a headmost point, and said electronic endoscope further comprises an illumination system that has at least two exit windows arranged around the entrance window of said objective lens system and light guide fiber bundles arranged on a light-source side of said at least two exit windows along said objective lens system as being curved to be convex toward said objective lens system.

12. An electronic endoscope according to claim 1, wherein said objective lens system includes a decentered lens and said solid-state image sensor is constructed to generate, at a center of said light receiving surface, a higher power in response to a light beam incident obliquely on said light-receiving surface than in response to a light beam incident perpendicularly on said light receiving surface.

13. An electronic endoscope according to any one of claims 1–3, wherein said solid-state image sensor is provided with members for condensing light on light-incidence sides of said pixels, respectively, and an amount of light condensed by said members increases progressively in going from a center of said solid-state image sensor to a periphery thereof.

14. An electronic endoscope according to any one of claims 1–3, wherein said solid-state image sensor is provided with microlenses on light-incidence sides of said pixels, respectively, and an optical axis of each of said microlenses is increasingly shifted from a center of each of said pixels in going from a middle of an object image projected on said solid-state image sensor to a periphery thereof.

15. An electronic endoscope according to any one of claims 1–3, wherein said solid-state image sensor is provided with microlenses on light-incidence sides of said pixels, respectively, and a diameter of each of said microlenses is enlarged progressively in going from a middle of an object image projected on said solid-state image sensor to a periphery thereof.

16. An electronic endoscope according to claim 12, wherein said solid-state image sensor is provided with microlenses on light-incidence sides of said pixels, respectively, and an optical axis of each of said microlenses is shifted, increasingly in going to one side of said solid-state image sensor and decreasingly in going to a remaining side thereof, from a center of each of said pixels at a middle of an object image projected on said solid-state image sensor.

17. An electronic endoscope according to claim 1, wherein said objective lens system includes three or less lenses, or three or less lens units, and satisfies the following condition:

$$1.5 < L/f < 4$$

where L is an equivalent air length from an exit pupil to an image plane and f is a focal length.

18. An electronic endoscope according to claim 17, wherein said objective lens system satisfies the following condition:

$$L'/f < 1.5$$

where L' is an equivalent air length from the exit pupil to an aperture stop.

19. An electronic endoscope according to claim 1, wherein said objective lens system includes, in order from an object side, a first lens unit, a second lens unit, and a third lens unit, said third lens unit being comprised of a cemented lens whose interface is convex toward an image side.

20. An electronic endoscope according to claim 1, wherein said objective lens system includes a lens or plane-parallel plate cemented to a CCD glass cover and satisfies the following condition:

$$\phi/2 < 1.2 \times IH$$

where $\phi$ is an outside diameter of said lens or plane-parallel plate cemented to said CCD glass cover and IH is a maximum image height.

21. An electronic endoscope, comprising:
an objective lens system defining an optical axis;
an image sensor comprising a plurality of sensing elements, said image sensor being arranged to intersect said optical axis and adapted to receive light rays from said objective lens system, wherein a first sensing element Of said plurality of sensing elements has a position closer to said optical axis than a second sensing element of said plurality of sensing elements, and wherein said second sensing element is more sensitive to said light rays than said first sensing element.

* * * * *

UNITED STATES PATENT AND TRADEMARK OFFICE
CERTIFICATE OF CORRECTION

PATENT NO.   : 6,476,851 B1
DATED        : November 5, 2002
INVENTOR(S)  : Nakamura It is certified that error appears in the above-identified patent and that said Letters Patent is hereby corrected as shown below:

<u>Title page,</u>
Item [56], References Cited, U.S. PATENT DOCUMENTS,
5,177,605 A    1/1993    "Takahashi et all." change to -- Takahashi et al. --
5,704,896 A    1/1998    "Fukunishi et at." change to -- Fukunishi et al. --
6,211,916 B1   4/2001    "Hawkins het al" change to -- Hawkins et al. --

FOREIGN PATENT DOCUMENTS, add the following reference:
-- EP     0,562,657     9/1993 --

Signed and Sealed this

Twenty-sixth Day of August, 2003

JAMES E. ROGAN
*Director of the United States Patent and Trademark Office*